US010975376B2

(12) United States Patent
Nakano et al.

(10) Patent No.: US 10,975,376 B2
(45) Date of Patent: Apr. 13, 2021

(54) PROTEIN EXPRESSION METHOD

(71) Applicant: National University Corporation Nagoya University, Nagoya (JP)

(72) Inventors: Hideo Nakano, Nagoya (JP); Teruyo Kato, Nagoya (JP)

(73) Assignee: National University Corporation Nagoya University, Nagoya (JP)

( * ) Notice: Subject to any disclaimer, the term of this patent is extended or adjusted under 35 U.S.C. 154(b) by 562 days.

(21) Appl. No.: 15/735,804

(22) PCT Filed: Jun. 15, 2016

(86) PCT No.: PCT/JP2016/067853
§ 371 (c)(1),
(2) Date: Dec. 12, 2017

(87) PCT Pub. No.: WO2016/204198
PCT Pub. Date: Dec. 22, 2016

(65) Prior Publication Data
US 2020/0032275 A1    Jan. 30, 2020

(30) Foreign Application Priority Data
Jun. 16, 2015  (JP) ................. 2015-121443

(51) Int. Cl.
C12N 15/70        (2006.01)
C12N 15/81        (2006.01)
C12P 21/00        (2006.01)

(52) U.S. Cl.
CPC ............. *C12N 15/70* (2013.01); *C12N 15/81* (2013.01); *C12P 21/00* (2013.01)

(58) Field of Classification Search
None
See application file for complete search history.

(56) References Cited

U.S. PATENT DOCUMENTS

| 5,153,120 | A | 10/1992 | Katsumata et al. |
| 5,714,575 | A | 2/1998 | Inouye et al. |
| 5,789,228 | A | 8/1998 | Lam et al. |
| 2010/0041153 | A1* | 2/2010 | Woldike .............. C12N 15/70 435/471 |
| 2012/0070868 | A1 | 3/2012 | Lee et al. |

FOREIGN PATENT DOCUMENTS

| JP | H03-232486 | A | 10/1991 |
| JP | H06-292582 | A | 10/1994 |
| JP | H08-070873 | A | 3/1996 |
| JP | 2000-512842 | A | 10/2000 |
| JP | 2014-526262 | A | 10/2014 |
| WO | 2008/104513 | A1 | 9/2008 |
| WO | 2012/048856 | A1 | 4/2012 |
| WO | 2012/109788 | A1 | 8/2012 |

OTHER PUBLICATIONS

Office Action dated Dec. 17, 2019, issued for the Japanese patent application No. 2017-525271 and English translation thereof.
German L. Rosano et al., "Recombinant protein expression in *Escherichia coli*: advances and challenges," Frontiers in Microbiology, Apr. 2014, vol. 5, Article 172, pp. 1-17. (disclosed in the spec).
Louis Bivona et al., "Influence of the second amino acid on recombinant protein expression," Protein Expr. Purif,. 2010; 74, pp. 248-256. (disclosed in the spec).
Daniel B. Goodman et al., "Causes and Effects of N-Terminal Codon Bias in Bacterial Genes," Siencexpress 2013, 10.1126/science. 1241934, 7 pages. (disclosed in the spec).
International Search Report dated Aug. 16, 2016, issued for PCT/JP2016/067853. (disclosed in the spec).
European Search Report dated Sep. 28, 2018, issued for the European patent application No. 16811672.1.
Yohei Sugano et al., "Introduction of amino acid residues at the N-terminus of the zeocin-resistance protein increases its expression in *Saccharomyces cerevisiae*", Biotechnology Letters, Springer Netherlands, Dordrecht, vol. 32, No. 10, Jun. 18, 2010, pp. 1515-1521. (cited in the Sep. 28, 2018 Search Report issued for EP16811672.1).
R. Shemesh et al., "Follow the Leader: Preference for Specific Amino Acids Directly Following the Initial Methionine in Proteins of Different Organisms", Genomics Proteomics and Bioinformatics, Beijing Genomics Institute, Beijing, CN, vol. 8, No. 3, Sep. 1, 2010, pp. 180-189. (cited in the Sep. 28, 2018 Search Report issued for EP16811672.1).
A. Tats et al., "Highly expressed proteins have an increased frequency of alanine in the second amino acid position", BMC Genomics, Biomed Central, vol. 7, No. 1, Feb. 16, 2006, pp. 1-13. (cited in the Sep. 28, 2018 Search Report issued for EP16811672.1).
Shim J-H, et al. , "Improvement of the Expression Level of beta-Glucosidase from *Agrobacterium* sp. In *Escherichia coli* by Rare Codon Optimization," Food Science and Biotechnology, 2013; 22:, pp. 269-273. (discussed in the spec).
Hirotaka Abo et al., "Influence of 5'-terminal region sequence of target gene on *Escherichia coli* expression system", Presentation No. 3B41p18, The 2015 Annual Meeting of the JSBBA in Okayama and machine English translation thereof. (discussed in the spec).
Yuying Shuai et al., "Purification and Characterization of gamma-Glutamyltranspeptidase from Bacillus subtilis SK 11.004", Journal of Agricultural and Food Chemistry, vol. 59, No. 11, Jun. 8, 2011, pp. 6233-6238, XP055673974. (cited in the Apr. 6, 2020 Office Action issued for EP16811672.1).
Office Action dated Apr. 6, 2020, issued for European Patent Applicatio No. 16811672.1.

* cited by examiner

*Primary Examiner* — Nancy J Leith
(74) *Attorney, Agent, or Firm* — Locke Lord LLP

(57) ABSTRACT

The present invention is intended to provide a highly versatile and simple technique which can increase the expression level of a protein in an *E. coli* expression system or a yeast expression system. Using an *E. coli* expression system or a yeast expression system, a target protein is expressed as a tag-added protein to which a peptide tag composed of an amino acid sequence SK, SKX, SKXX (SEQ ID NO. 1), AKXX (SEQ ID NO. 29), or KKXX (SEQ ID NO. 30) (wherein X represents any amino acid residue) is linked at the N-terminal.

20 Claims, 12 Drawing Sheets

Specification includes a Sequence Listing.

PROTEIN EXPRESSION METHOD

TECHNICAL FIELD

The present invention relates to a protein expression method, and specifically to a novel expression method which allows the increase of the expression level of a protein, and the uses of the method. This application claims the benefit of priority from prior Japanese Patent Application No. 2015-121443, filed on Jun. 16, 2015, the entire contents of the patent application are incorporated herein by reference.

BACKGROUND ART

In the expression of recombinant proteins, *E. coli* and yeasts are most frequently used attractive hosts. Various expression vectors and promoters for expressing target proteins have been developed (Non Patent Literature 1).

Expression systems using *E. coli* as hosts have been used since long ago, and provide high versatility thanks to their ease in handling. However, depending on the protein to be expressed, the expression level in the soluble form may be small. In addition to the problem of solubility, the expression level itself is small, so that the expression of proteins, regardless of solubility, may not be detected.

There are many reports on the difference among proteins, but the cause has not been clarified. Various theories are proposed, and there is a report that the difference was made by the difference in stability of mRNA and the amino acid following the initiation codon (Non Patent Literature 2). There are other theories that the sequence upstream of the initiation codon is important, and that the codon is important (Non Patent Literature 3).

Because of these problems, the attempts to increase the expression levels of recombinant proteins generally require cumbersome operations such as (1) conversion of the codon, (2) expression after fusion with other highly soluble protein, (3) change of the culture medium, (4) co-expression with a chaperone factor, and (5) change of the expression system (host-vector).

Typical examples relating to the above-described attempts are as follows. Firstly, the codon conversion is carried out by, for example, conversion of rare codons in *E. coli* to those appropriate for *E. coli* (Non Patent Literature 4). In addition, recombinant strains having reinforced tRNA genes corresponding to rare codons are increasingly used.

The fusion expression with another highly soluble protein uses, for example, glutathione-S-transferase (GST), a maltose biding domain, a Trx (thioredoxin) tag, or a SUMO (small ubiquitin-like modifier) tag, which are already known to be soluble and achieve a high expression in *E. coli*. However, according to this method, the target protein is expressed in the state fused with another protein which is intrinsically unnecessary, so that the operation for cutting of the target protein is required. Furthermore, it is unfavorable in terms of the production cost to make the host produce intrinsically unnecessary matter.

The change of the culture medium is carried out by, for example, replacing an LB culture medium, which is generally used for culturing *E. coli*, with a more nutrient medium such as Super Broth, Terrific Broth, or MMI broth.

In addition, host vector systems are actively studied, and the improvement in the expression level is attempted by using a promoter such as T7, acUV5, tac, λPL, lac, trp, or cspA, or combining the hosts which are more suitable for protein expression.

It is also a known attempt that a base sequence composed of about 40 bases is inserted at the N-terminal or in the upstream part of the initiation codon, thereby increasing the expression level (Non Patent Literature 5). In addition, there is a study report on the trend of the N-terminal sequences of proteins showing high expression levels in *E. coli* (Non Patent Literature 6).

In addition to the expression system using *E. coli* as a host, an expression system using a yeast as a host is also used for expression of various proteins.

CITATION LIST

Non Patent Literature 1: German and Eduardo. Front Microbiol. 2014; 5: 172

Non Patent Literature 2: Bivona et al. Protein Expr. Purif. 2010. 74. 248-256.

Non Patent Literature 3: Siencexpress 2013.10.1126/science. 1241934

Non Patent Literature 4: Food Science and Biotechnology, 2013, 22, 269

Non Patent Literature 5: 2015 Japan Society for Bioscience (Okayama pref.), lecture No. 3 B41 p. 18, Abo et al.

Non Patent Literature 6: Bivona et al. Protein Expr. Purif. 2010. 74. 248-256.

SUMMARY OF THE INVENTION

Technical Problem

As described above, there are an infinite number of study reports aimed at the increase of the expression levels of proteins. However, in spite of the above-described studies, the expression level is not necessarily increased, and clear rules for increasing the expression level have not been found. Accordingly, the present invention is intended to provide a highly versatile and simple technique which can increase the expression level of a protein in an *E. coli* expression system or a yeast expression system.

Solution to Problem

In view of the above-described problems, the inventors carried out studies aimed at the creation of the method for increasing the expression level by simple operations without changing the host or vector system. As a result of dedicated research, it was found that the expression level of a target protein in *E. coli* can be markedly increased only by inserting a tag composed of only four amino acids into the site immediately after the initiation codon (in other words, a target protein to which a tag composed of four amino acids is linked at the N-terminal is expressed). This method has advantages such as that (1) the peptide (tag) to be added is short, so that its possibility to affect the original activity of the target protein is likely extremely low, and (2) the method can be performed by simple operations (insertion can be easily performed by a molecular biological method such as a PCR method). In addition, by adding a protease recognition sequence to the region downstream of the tag, the necessary part (the peptide fragment containing the tag) can be separated from the target protein by protease treatment. The unnecessary part is usually markedly shorter than the target protein (the part is typically composed of several amino acid residues), and thus can be readily separated from the target protein (usually, the molecular weight is more than several kDa). On the other hand, the use of an antibody recognizing the tag allows purification of the expression product (tag-added target product) as it is.

As a result of further study, it was shown that the above-described method using a tag functioned effectively not only in an *E. coli* expression system, but also in a cell-free protein synthesis system. In addition, important findings were obtained regarding relationship between the length of the peptide composing the tag and the effect of increasing the expression level. Furthermore, it was proved that the above-described method was effective also in a yeast expression system which was frequently used, just like an *E. coli* expression system.

The further study succeeded in finding another tag which was effective for increasing the expression level.

On the basis of the above findings, the invention described below is provided.

[1] A protein expression method including expressing a target protein as a tag-added protein to which a peptide tag composed of an amino acid sequence SK, SKX, SKXX (SEQ ID NO. 1), AKXX (SEQ ID NO. 29), or KKXX (SEQ ID NO. 30) (wherein X represents any amino acid residue) is linked at the N-terminal by an *E. coli* expression system or a yeast expression system.

[2] The expression method of [1], wherein the peptide tag is composed of an amino acid sequence SKI, SKIK (SEQ ID NO. 3), SKKK (SEQ ID NO. 32), SKII (SEQ ID NO. 31), AKIK (SEQ ID NO. 33), AKII (SEQ ID NO. 34), or KKKK (SEQ ID NO. 35).

[3] The expression method of [1] or [2], wherein the peptide tag and the sequence of the target protein are directly linked together.

[4] The expression method of [1] or [2], wherein a protease recognition sequence is sandwiched between the peptide tag and the target protein sequence.

[5] The expression method of any one of [1] to [4], wherein the *E. coli* expression system is an expression system using a T7 promoter or a low temperature expressing promoter.

[6] The expression method of any one of [1] to [5], which includes the following steps (1) to (3):

(1) a step of providing an expression vector holding a sequence coding a target protein to which the peptide tag is linked at the N-terminal;

(2) a step of introducing the expression vector into a host cell; and (3) a step of culturing a transformant into which the expression vector has been introduced, thereby expressing the target protein.

[7] The expression method of [6], wherein the expression vector is constructed by any of the following methods (a) to (c):

(a) inserting a sequence coding a target protein, to which a peptide tag is linked, into the vector for expressing the host cell;

(b) inserting a sequence coding a target protein by in-frame into a vector for expressing the host cell having a sequence coding the peptide tag immediately after the initiation codon, downstream from the sequence; or (c) inserting a sequence coding a peptide tag immediately after the initiation codon of the vector for expressing the host cell holding the sequence coding the target protein.

[8] The expression method of any one of [1] to [5], wherein the *E. coli* expression system is a cell-free protein synthesis system using an *E. coli*-derived component.

[9] The expression method of [8], which includes the following steps (i) and (ii):

(i) a step of providing a template for expression containing a sequence coding the target protein to which the peptide tag is linked at the N-terminal; and (ii) a step of conducting a cell-free protein synthesis.

[10] An expression vector for an *E. coli* expression system, including:

a promoter functioned in *E. coli*;

a ribosome binding site;

an initiation codon;

a sequence coding a peptide tag composed of an amino acid sequence SK, SKX, SKXX (SEQ ID NO. 1), AKXX (SEQ ID NO. 29), or KKXX (SEQ ID NO. 30) (wherein X represents any amino acid residue), which is placed immediately after the initiation codon; and a cloning site placed downstream of the sequence.

[11] An expression vector for a yeast expression system, including:

a promoter functioned by a yeast;

an initiation codon;

a sequence coding a peptide tag composed of an amino acid sequence SK, SKX, SKXX (SEQ ID NO. 1), AKXX (SEQ ID NO. 29), or KKXX (SEQ ID NO. 30) (wherein X represents any amino acid residue), which is placed immediately after the initiation codon; and a cloning site placed downstream of the sequence.

[12] The expression vector of [10] or [11], wherein the sequence coding a peptide tag and the cloning site are adjacent to each other.

[13] The expression vector of [10] or [11], wherein a sequence coding a protease recognition sequence is placed between the sequence coding a peptide tag and the cloning site.

[14] An expression vector for an *E. coli* expression system, comprising:

a promoter functioned in *E. coli*;

a ribosome binding site;

an initiation codon;

a sequence coding a peptide tag composed of an amino acid sequence SK, SKX, SKXX (SEQ ID NO. 1), AKXX (SEQ ID NO. 29), or KKXX (SEQ ID NO. 30) (wherein X represents any amino acid residue), which is placed immediately after the initiation codon; and a sequence coding a target protein placed downstream of the sequence.

[15] An expression vector for a yeast expression system, including:

a promoter functioned in a yeast;

an initiation codon;

a sequence coding a peptide tag composed of an amino acid sequence SK, SKX, SKXX (SEQ ID NO. 1), AKXX (SEQ ID NO. 29), or KKXX (SEQ ID NO. 30) (wherein X represents any amino acid residue), which is placed immediately after the initiation codon; and a sequence coding a target protein placed downstream of the sequence.

[16] A kit for expressing a target protein, including the expression vector of any one of [10] to [15].

[17] The kit of [16], which further includes an antibody recognizing the peptide tag linked to the N-terminal of a protein.

[18] The kit of [17], wherein the antibody is supported by an insoluble support or a magnetic material.

[19] The kit of any one of [16] to [18], which further includes a peptide having the peptide tag at the N-terminal.

[20] The kit of [19], wherein the peptide is composed of an amino acid sequence SK, SKX, SKXX (SEQ ID NO. 1), AKXX (SEQ ID NO. 29), or KKXX (SEQ ID NO. 30) (wherein X represents any amino acid residue).

[21] A recombinant protein to which a peptide tag composed of an amino acid sequence SK, SKX, SKXX (SEQ ID NO. 1), AKXX (SEQ ID NO. 29), or KKXX (SEQ ID NO. 30) (wherein X represents any amino acid residue) is linked at the N-terminal.

Figure 4:
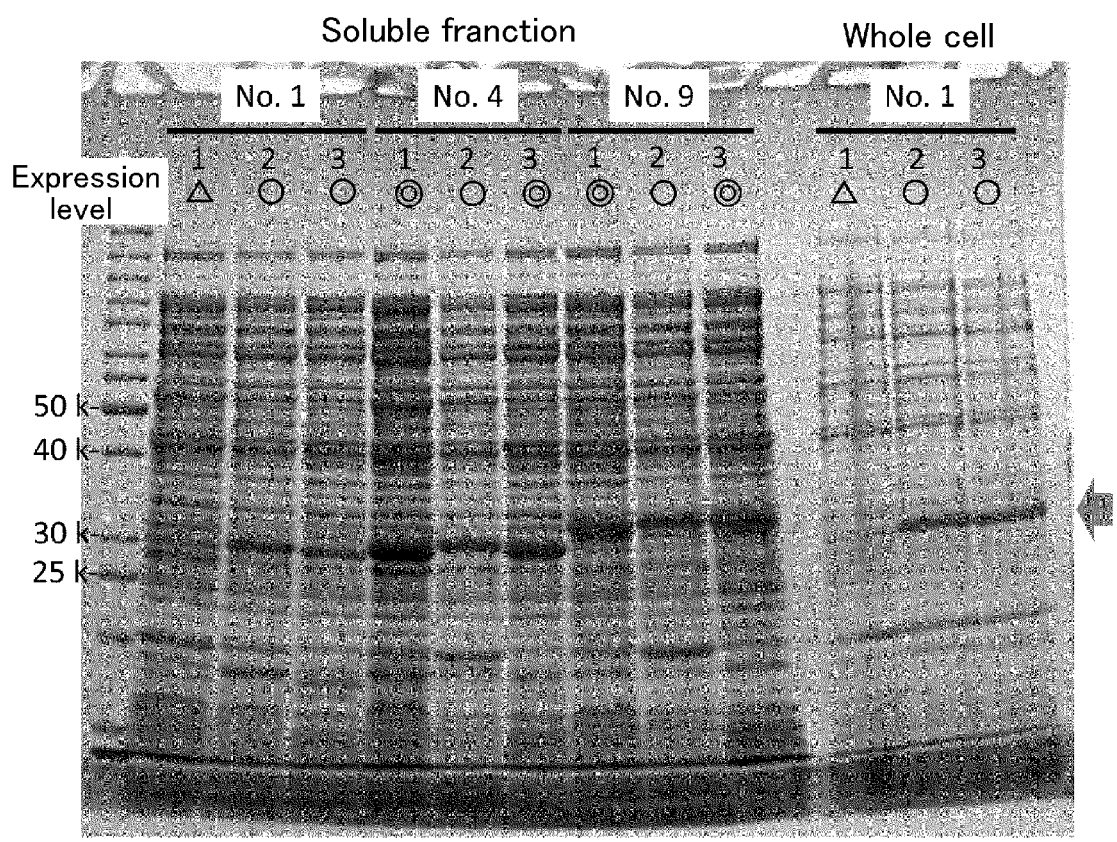

FIG. 4 shows the comparison between the T7 tag and the SKIK tag (SEQ ID NO. 3) in the result of SDS-PAGE on the expression product. The arrow represents the size of the target protein. The expression level was rated on a scale of .circle-w/dot., .largecircle., .DELTA., and x based on the density of the band of the target protein size. 1: no tag, 2: T7 tag, and 3: SKIK tag (SEQ ID NO. 3).

Figure 5:
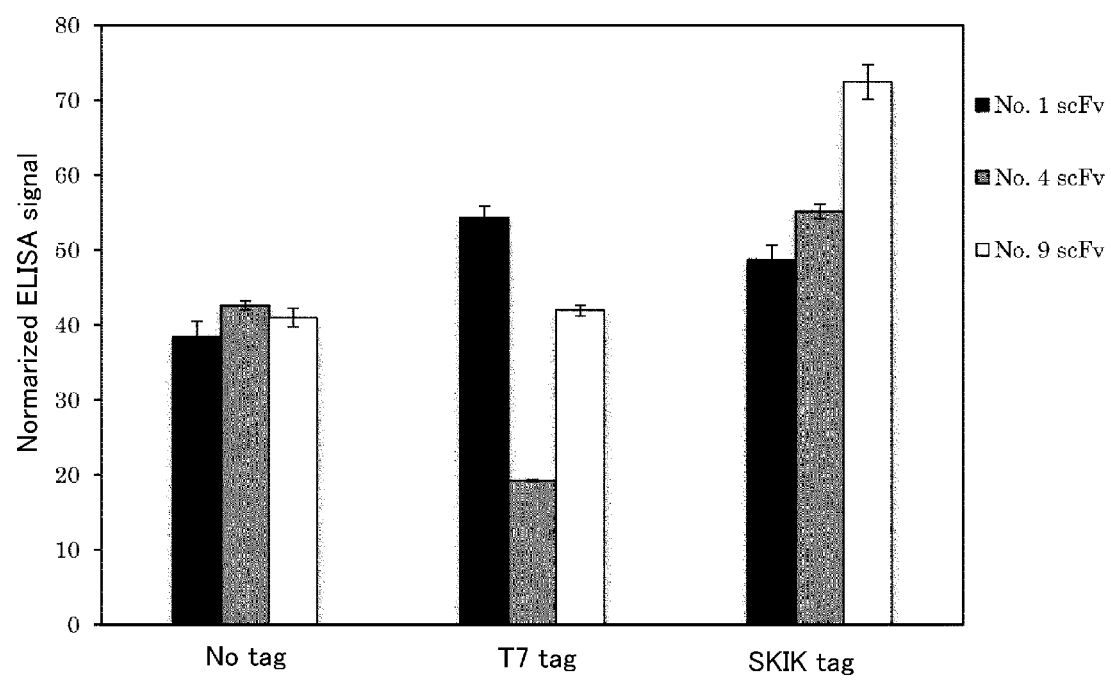

FIG. 5 shows the comparison between the T7 tag and the SKIK tag (SEQ ID NO. 3). The tag-added scFvs were purified from the expression products, and the reactivity for the antigen was studied by ELISA. The value obtained by dividing the ELISA signal by the protein concentration was used for the comparison and evaluation.

Figure 6:
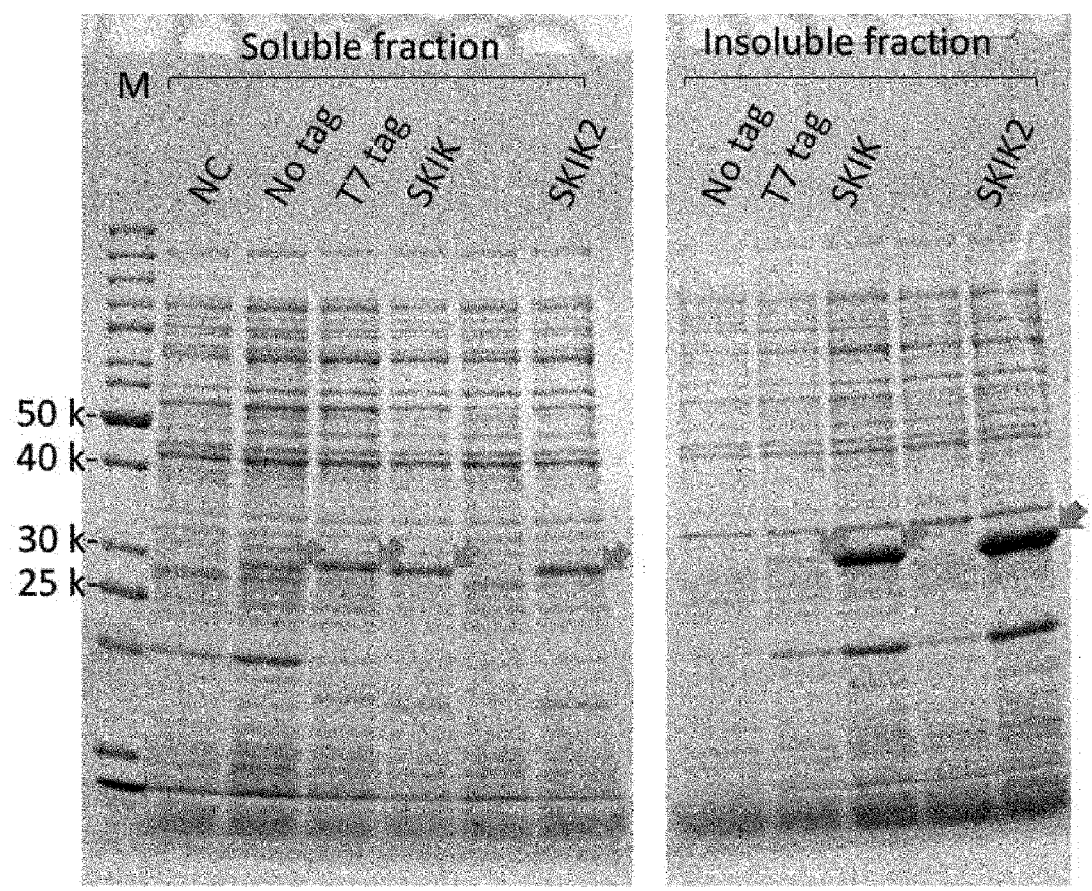

FIG. 6 shows the influence of the codon on the effect of SKIK (SEQ ID NO. 3) in the result of SDS-PAGE on the expression product (CBB staining).

Figure 7:
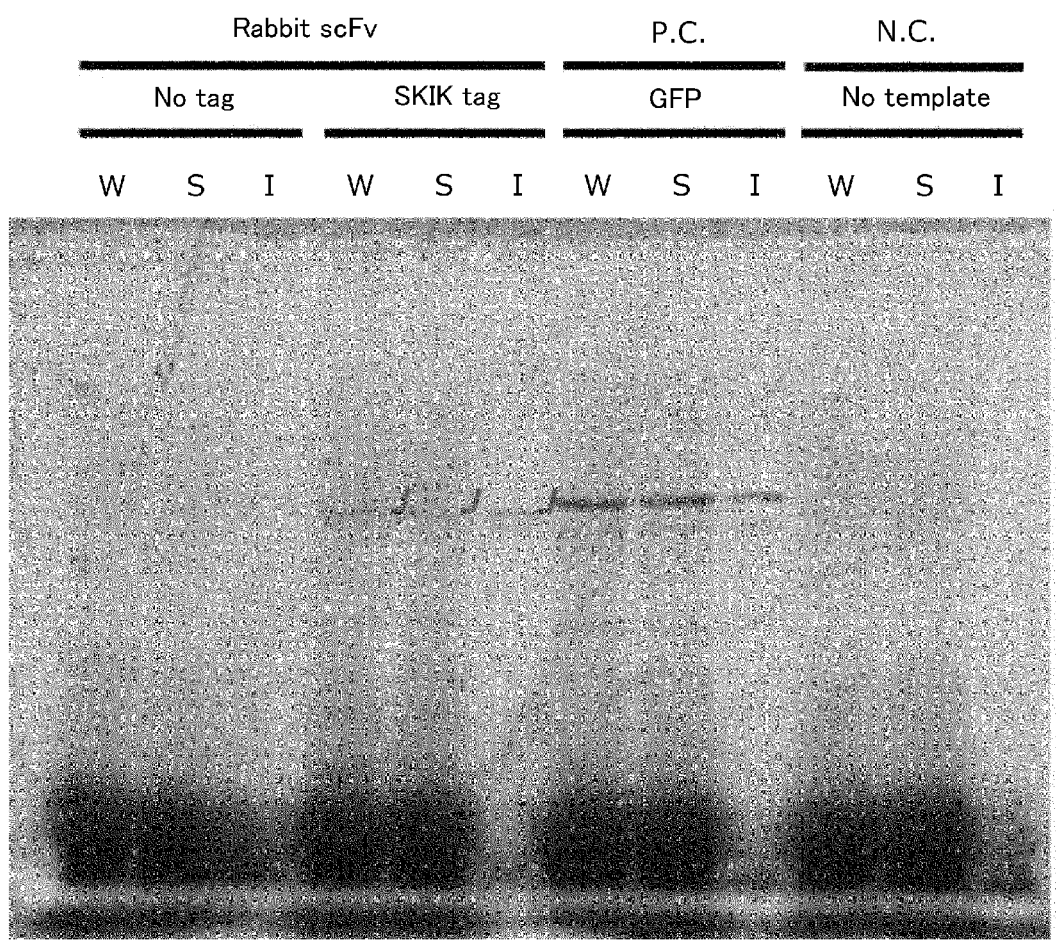

FIG. 7 shows the tag effect in a cell-free synthesis system in the result of fluorescence detection on the gel after SDS-PAGE. W: whole cell (Whole), S: soluble fraction (soluble), and I: insoluble fraction (insoluble).

Figure 8:
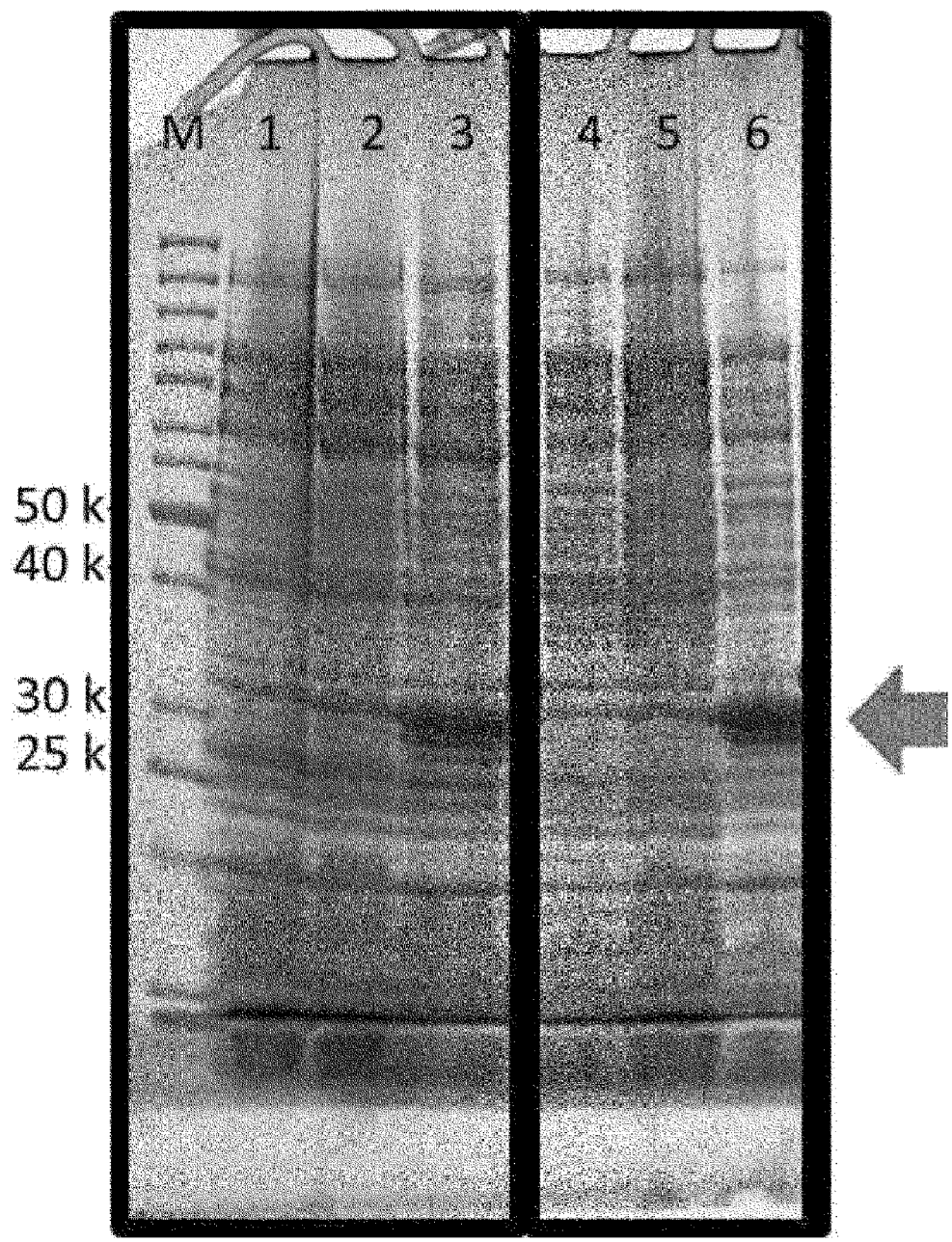

FIG. 8 shows the influence of the control promoter in the result of SDS-PAGE (CBB staining). M: marker (Thermo ladder), lane 1: pET22b, lane 2: no pET22b-m6FabLZ tag, lane 4: pET22b-m6FabLZ SKIK (SEQ ID NO. 3), lane 4: pColdI, lane 5: no pCold-m6FabLZ tag, and lane 6: pCold-m6FabLZ SKIK (SEQ ID NO. 3).

Figure 9:
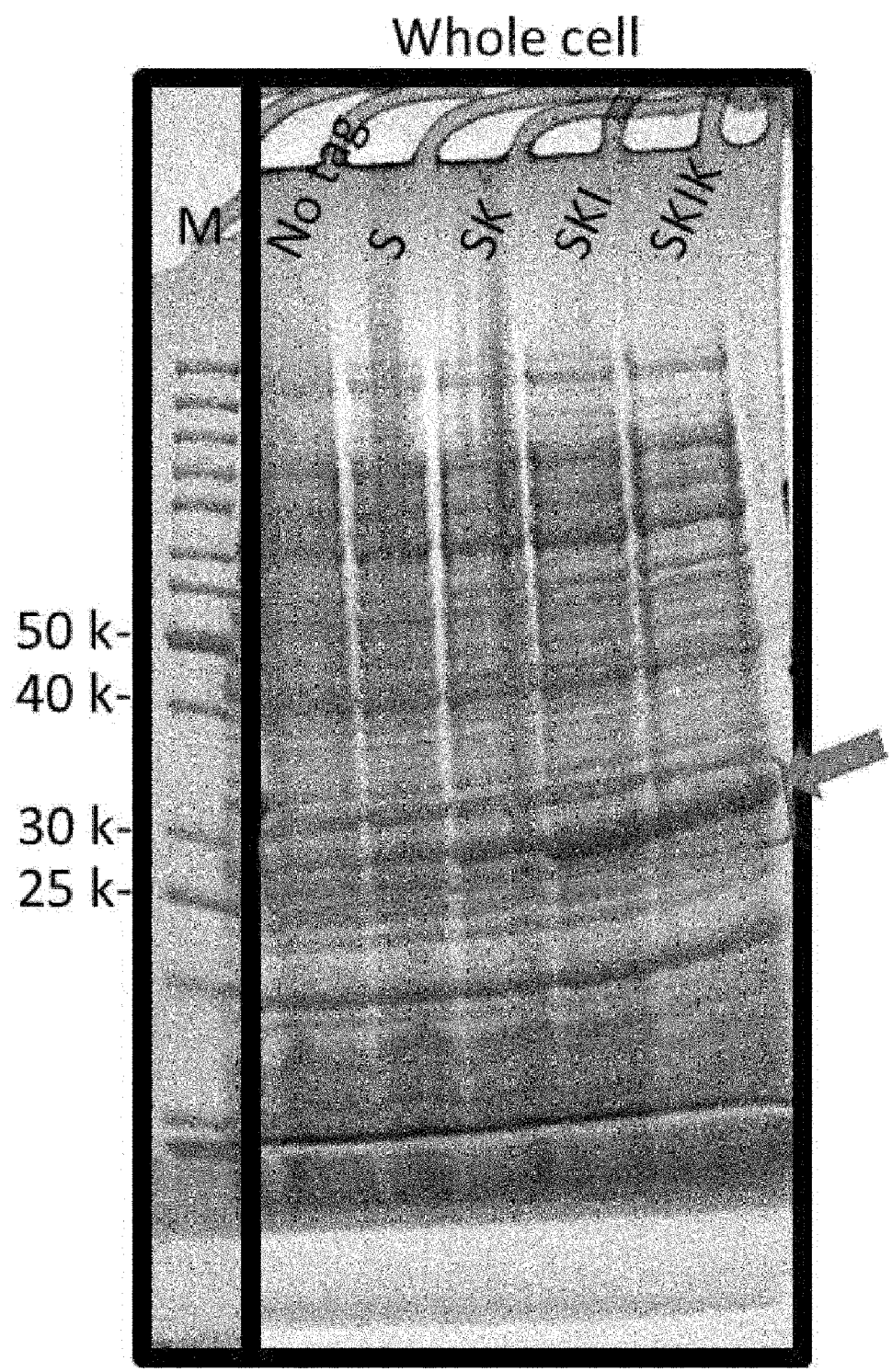

FIG. 9 shows the study of the tag length in the result of SDS-PAGE (CBB staining).

Figure 10:
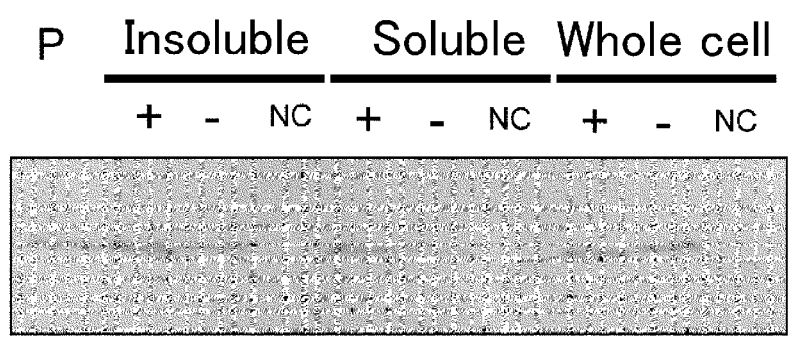
Figure 11:
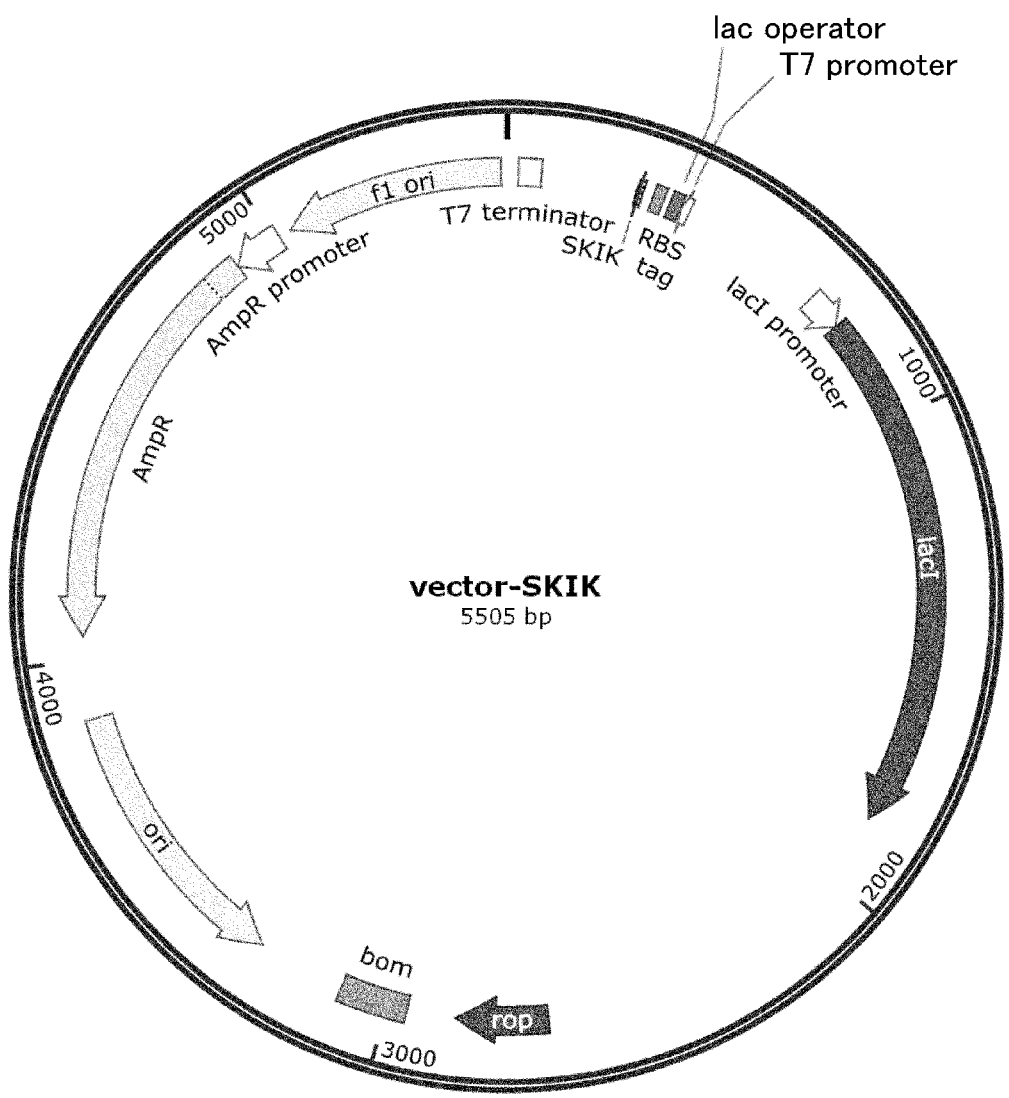

FIG. 10 shows the effect in a yeast expression system. P: r4scFv purification product expressed by the *E. coli* Shuffle T7 express. +: SKIK tag (SEQ ID NO. 3), −: No tag, NC: pYC2/NT empty vector expression product FIG. 11 shows an example of the vector into which the SKIK tag (SEQ ID NO. 3) is incorporated.

Figure 12:
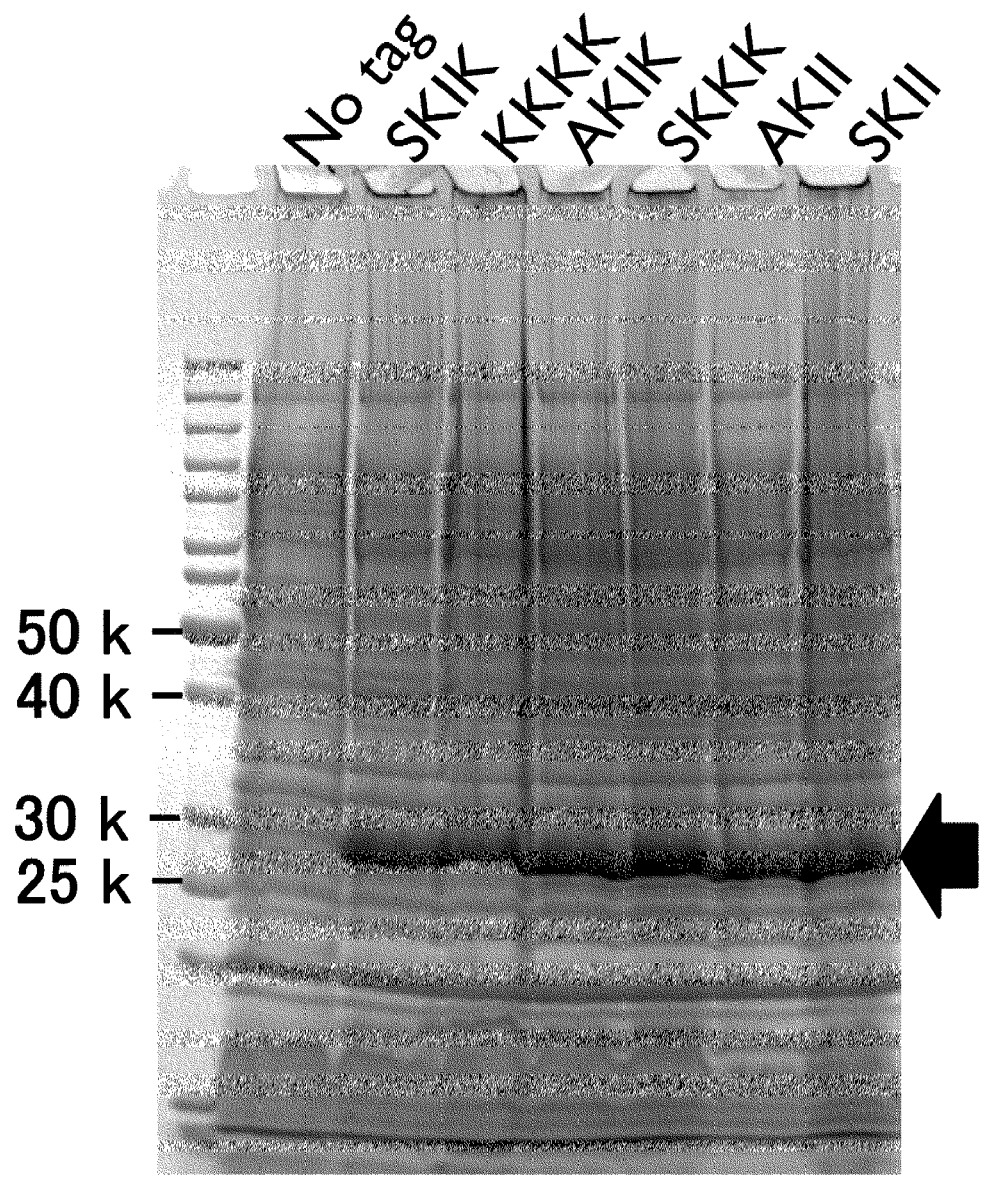

FIG. 12 shows the effect of another tag in the result of SDS-PAGE (CBB staining).

DESCRIPTION OF EMBODIMENTS

1. Protein Expression Method

A first aspect of the present invention relates to a protein expression method. In the present invention, a target protein is expressed by an *E. coli* expression system or yeast expression system. The "*E. coli* expression system" collectively describes the expression systems using *E. coli* as the host (referred to "*E. coli* expression system" according to convention) and cell-free protein synthesis systems using *E. coli*-derived components. The yeast expression system is an expression system using yeast cells as the host.

The greatest feature of the present invention is that the target protein is expressed as a protein to which a specific peptide tag (hereinafter referred to as "the peptide tag of the present invention") is linked at the N-terminal (tag-added protein).

The peptide tag of the present invention is composed of an amino acid sequence SK, SKX, SKXX (SEQ ID NO. 1), AKXX (SEQ ID NO. 29), or KKXX (SEQ ID NO. 30). X represents any amino acid residue. The X following SK is, for example, I (Ile), K (Lys), S (Ser), or A (Ala). In the same manner, the X following SKX is, for example, K (Lys) or I (Ile). The X following AK is preferably I (Ile). The X following AKX is preferably I (Ile) or K (Lys). The X following KK is preferably K (Lys). The X following KKX is preferably K (Lys).

SK is a peptide (Ser-Lys) composed of serine (Ser) and lysine (Lys) linked in this order from the N-terminal side toward the C-terminal side. SKX is a peptide formed by adding an amino acid residue to SK, and SKXX (SEQ ID NO. 1) is a peptide formed by adding two amino acid residues to SK. A specific example of the peptide represented by SKX is SKI (Ser-Lys-Ile). SKXX (SEQ ID NO. 1) is preferably SKIX (SEQ ID NO. 2). In other words, it preferably contains SKI. Specific examples of the peptide represented by SKIX (SEQ ID NO. 2) are SKIK (Ser-Lys-Ile-Lys) (SEQ ID NO. 3) and SKII (Ser-Lys-Ile-Ile) (SEQ ID NO. 31). SKKK (Ser-Lys-Lys-Lys) (SEQ ID NO. 32) is also one of preferable specific examples.

AKXX (SEQ ID NO. 29) is a peptide formed by adding two amino acid residues to the peptide (Ala-Lys), which is composed of alanine (Ala) and lysine (Lys) linked in this order from the N-terminal side toward the C-terminal side. Specific examples of the peptide represented by AKXX (SEQ ID NO. 29) are AKIK (Ala-Lys-Ile-Lys) (SEQ ID NO. 33) and AKII (Ala-Lys-Ile-Ile) (SEQ ID NO. 34).

KKXX (SEQ ID NO. 30) is a peptide formed by adding two amino acid residues to the peptide (Lys-Lys), which is composed of lysine (Lys) and lysine (Lys) linked in this order from the N-terminal side toward the C-terminal side. A specific example of the peptide represented by KKXX (SEQ ID NO. 30) is KKKK (Lys-Lys-Lys-Lys) (SEQ ID NO. 35).

As described above, the peptide tag of the present invention is composed of the amino acid sequence SK, SKX, SKXX (SEQ ID NO. 1), AKXX (SEQ ID NO. 29), or KKXX (SEQ ID NO. 30), and typically includes two to four amino acid residues. As long as its function (to improve the expression level of a target protein) will not be affected, other amino acid residue may be added to the N- and/or C-terminal side. In this embodiment, the entire length is from 5 to 13 amino acid residues, preferably from 5 to 10 amino acid residues, and more preferably from 5 to 7 amino acid residues.

The number of the above-described peptide tag (SK, SKX, SKXX (SEQ ID NO. 1), AKXX (SEQ ID NO. 29), or KKXX (SEQ ID NO. 30)) may be plural. For example, two to five of the peptide tags may be tandemly linked to. Alternatively, the peptide tag may be combined (linked) with another tag (for example, His tag, HA tag, or FLAG tag).

(1) Expression System Using Living Cells (*E. coli* Expression System, Yeast Expression System)

In the expression system using living cells (*E. coli* or a yeast), a host transformed by an expression vector holding the sequence coding the target protein (transformant) is cultured, whereby the target protein is expressed. Specifically, the target protein is expressed by the following steps (1) to (3).

(1) a step of providing an expression vector holding a sequence coding the target protein to which the peptide tag of the present invention is linked at the N-terminal;

(2) a step of introducing the expression vector into a host cell; and (3) a step of culturing the transformant into which the expression vector has been introduced, thereby expressing the target protein.

The step (1) is characteristic of the present invention, wherein an expression vector enabling the expression of a tag-added protein in a host is provided. The expression method of the present invention uses an expression vector holding the sequence coding the target protein to which the peptide tag of the present invention is linked at the N-terminal.

The expression vector when using *E. coli* as a host includes a promoter which functions in *E. coli*, a ribosome binding site, an initiation codon, the sequence coding the peptide tag of the present invention placed immediately after the initiation codon, the sequence coding the target protein placed downstream of the aforementioned sequence, thereby allowing expression of the target protein in *E. coli*. Typically, the expression vector is in the form of a plasmid.

The promoter will not be particularly limited as long as it functions in *E. coli*. For example, a T7 promoter, a lac promoter, a tac promoter, a trp promoter, a T3 promoter, an SP6 promoter, or a low temperature expression promoter (a promoter for the cold shock gene cspA) may be used. Among them, the T7 promoter and low temperature expression promoter are particularly preferred, because they are readily induced, and allow powerful expression control.

The ribosome binding site is located upstream of the initiation codon, and contains the sequence (SD sequence) to which ribosome binds. The SD sequence is rich in adenine and guanine, and is composed of, for example, the sequence AGGAGG.

The sequence coding the peptide tag is placed immediately after the initiation codon. Any sequence may be used as long as it codes a peptide tag. For example, the sequence tctaaa or tcg aag may be used for the peptide tag SK, the sequence tct aaa ata or tcg aag atc may be used for the peptide tag SKI, the sequence tct aaa ata aaa (SEQ ID NO. 4) or tcg aag atc aag (SEQ ID NO. 5) may be used for the peptide tag SKIK (SEQ ID NO. 3), the sequence tct aaa aaa aaa (SEQ ID NO. 37) may be used for the peptide tag SKKK (SEQ ID NO. 32), the sequence tct aaa att att (SEQ ID NO. 36) may be used for the peptide tag SKII (SEQ ID NO. 31), the sequence gca aaa att aaa (SEQ ID NO. 38) may be used for the peptide tag AKIK (SEQ ID NO. 33), the sequence gca aaa att att (SEQ ID NO. 39) may be used for the peptide tag AKII (SEQ ID NO. 34), and the sequence aaa aaa aaa aaa (SEQ ID NO. 35) may be used for the peptide tag KKKK (SEQ ID NO. 35).

The sequence coding the target protein is placed downstream of the sequence coding the peptide tag. The "target protein" is the protein to be produced by the expression method of the present invention. Examples of the target protein include those useful as components of medicines, food, or investigation reagents, such as enzymes (for example, amylase, isoamylase, lactase, glucose isomerase, cellulase, pectinase, invertase, hyaluronidase, pepsin, papain, trypsin, chymotrypsin, bromelain, thermolysin, lipase, urokinase, and urease), antibodies, antibody fragments, cytokines (for example, interferon and interleukin), hormones (erythropoietine, insulin, glucagon, secretin, gastrin, vasopressin, growth hormone, thyroid-stimulating hormone, prolactin, luteinizing hormone, follicle-stimulating hormone, adrenocorticotropic hormone, thyrotropin-releasing hormone, luteinizing hormone-releasing hormone, corticotrop[h]in-releasing hormone, growth hormone releasing-hormone, and somatostatin), opioide peptides (for example, endorphin, enkephalin, and dynorphin), and fibrous protein (for example, keratin, collagen, and elastin).

The sequence coding the peptide tag and the sequence coding the target protein are linked directly or via other sequence. An example of the other sequence is the sequence coding a protease recognition sequence. The protease recognition sequence is an amino acid sequence which is recognized by a specific protease, and necessary for cleaving a protein by the protease. For example, a sortase recognition sequence, an HRV3C recognition sequence, or a TEV protease recognition sequence may be used. Alternatively, not a functional sequence which codes a protease recognition sequence, but a sequence having no specific function may be sandwiched between the sequence coding the peptide tag and the sequence coding the target protein.

The expression vector may include, in addition to the above-described elements, for example, an element necessary for the proliferation in the host *E. coli*, an element necessary or useful for the expression of the target protein, and an element useful for detection and discrimination. Examples of the element which can be incorporated into the expression vector include a replication point, terminators (for example, a T7 terminator), drug resistance genes (for example, an ampicillin resistance gene, a kanamycin resistance gene, a chloramphenicol resistance gene, and a streptomycin resistance gene).

The expression vector having the above-described composition is constructed by, for example, any of the following (a) to (c):

(a) a method of inserting a sequence coding the target protein, to which the peptide tag of the present invention is linked, into the vector for *E. coli* expression;

(b) a method of inserting a sequence coding the target protein by in-frame into the vector for *E. coli* expression having the sequence coding the peptide tag of the present invention immediately after the initiation codon, downstream of the sequence; or (c) a method of inserting a sequence coding the peptide tag of the present invention immediately after the initiation codon of the vector for *E. coli* expression holding the sequence coding the target protein.

The construction method (a) uses the elements necessary for expression, such as a promoter and a ribosome binding site, and a vector having a cloning site. The cloning site is used for inserting the gene coding the target protein. The cloning site may be a multi-cloning site. The expression vector used for the expression method of the present invention is completed by inserting the sequence coding the target protein, to which the peptide tag of the present invention is linked, into the cloning site. An expression product composed of a peptide tag directly linked to the target protein can be obtained by forming a cloning site adjacent to the sequence coding the peptide tag. One of the advantages of this construction method is that commercially available general-purpose vectors can be used.

In the construction method (b), a vector, into which the sequence coding the peptide tag of the present invention has been incorporated, is used. A cloning site for inserting the sequence coding the target protein by in-frame is provided downstream of the sequence coding the peptide tag of the present invention. The expression vector used in the expression method of the present invention is completed by inserting the sequence coding the target protein into the cloning site. This construction method does not require the sequence coding the target protein to which the peptide tag of the present invention is linked (more specifically, the sequence coding the target protein can be used as it is). Accordingly, this is especially effective for, for example, expressing many kinds of target proteins. FIG. 11 shows the examples of the vector which can be used in the construction method (b).

The construction method (c) uses a vector holding the sequence coding the target protein, different from the above-described two construction methods. In this construction method, the sequence coding the peptide tag of the present invention is inserted immediately after the initiation codon of the vector, whereby the expression vector used in the expression method of the present invention is completed. The peptide tag of the present invention is inserted in such a manner that the sequence coding the peptide tag and the sequence coding the target protein are linked by in-frame. This construction method is especially effective when the vector holding the sequence coding the target protein is available (for example, when the vector is already owned (constructed or acquired), or easily available).

An expression vector for obtaining an expression product, which is composed of a protease recognition sequence sandwiched between a peptide tag sequence and a target protein sequence, is obtained as follows: in the construction method (a), the sequence to be inserted is a sequence coding a protease recognition sequence sandwiched between the peptide tag of the present invention and the sequence coding the target protein; in the construction method (b), for example, the vector for *E. coli* expression to be used is composed of a sequence coding a protease recognition sequence in the downstream part of the sequence coding the peptide tag of the present invention; and in the construction method (c), for example, a sequence coding the protease recognition sequence is inserted together with the peptide tag of the present invention.

Many expression vectors which can be used for the *E. coli* expression system have been developed, and the expression vector of the present invention can be constructed using an existing expression vector.

The expression vector provided in the step (1) is introduced into the host *E. coli* (step (2)). This introduction operation may be performed in an ordinary method. For example, the expression vector can be introduced by a competent cell method (for example, a calcium chloride method, a rubidium chloride method, a Hanahan method, or an SEM method), or an electroporation method. Examples of the host *E. coli* include a JM109 strain, an MC1061 strain, a DH5α strain, and a BL21 strain.

In the step (3) following the step (2), a transformed *E. coli* (transformant), into which an expression vector has been introduced, is cultured, and the target protein is expressed. The culture conditions are not particularly limited as long as they grow the transformant and express the target protein. The standard culture conditions may be modified as necessary. In addition, appropriate culture conditions can be established by a preliminary experiment.

The composition of the culture medium is not particularly limited. Examples of the carbon source for the culture medium include maltose, sucrose, genthiobiose, soluble starch, glycerol, dextrin, molasses, and organic acids. Examples of the nitrogen source include ammonium sulfate, ammonium carbonate, ammonium phosphate, ammonium acetate, peptone, yeast extract, corn steep liquor, casein hydrolysate, bran, and meat extracts. Examples of the inorganic salt include potassium salts, magnesium salts, sodium salts, phosphates, manganese salts, iron salts, and zinc salts. In order to accelerate the growth of a recombination fungi, a culture medium containing vitamins and amino acids may be used.

When the promoter is an inductive one, expression of the target protein is induced by adding an inducing factor (inducer) to the culture medium, or changing the culture conditions. The inducing factor is chosen according to the type of the promoter to be used. Examples of the inducing factor include isopropyl-1-thio-β-D-galactoside (IPTG) and indoleacetic acid (IAA).

The target protein is collected from the culture solution or bacterial cells. When it is collected from the culture solution, the culture supernatant is subjected to filtration or centrifugation treatment for removing insoluble matter, and then the target protein is obtained through separation and purification performed by appropriately combining concentration using an ultrafiltration membrane, salting out of ammonium sulfate precipitate and others, dialysis, and various types of chromatography. On the other hand, when the target protein is collected from bacterial cells, for example, the bacterial cells are crushed by pressurization, ultrasonication, or bead crushing, and then separation and purification are carried out in the same manner as described above, whereby the target protein is obtained. The above-described series of processes (crushing of bacterial cells, separation, and purification) may be carried out after collecting the bacterial cells from the culture solution by filtration or centrifugation.

According to the above-described method, the target protein (tag-added protein) to which the peptide tag of the present invention is linked at the N-terminal is obtained as an expression product. In one embodiment, the expression product is composed of the peptide tag of the present invention directly linked to the target protein (more specifically, no amino acid/amino acid sequence is present between the peptide tag of the present invention and the target protein sequence). When an expression vector containing a sequence coding a protease recognition sequence is used, an expression product composed of the protease recognition sequence sandwiched between the peptide tag of the present invention and the target protein sequence is obtained. In this embodiment, the target protein cut (separated) from the peptide tag can be obtained by subjecting the expression product to protease treatment.

On the other hand, the case using a yeast expression system (more specifically, the expression method using a yeast as the host) is conducted in the same manner as the above-described case using an *E. coli* expression system. Accordingly, the corresponding explanations for the *E. coli* expression system are cited unless otherwise specified.

The expression vector when the host is a yeast includes a promoter which functions in the yeast, an initiation codon, the sequence coding the peptide tag of the present invention placed immediately after the initiation codon, and the sequence coding the target protein placed downstream of the aforementioned sequence, thereby allowing expression of the target protein in the yeast. Typically, the expression vector is in the form of a plasmid. It may be a shuttle vector having an origin of replication which can be replicated in *E. coli*.

Examples of the plasmid when using a yeast as a host include those including GAL1, GAL10, AOX1, pTEF1, pADH1, pTPI1, pHXT7, pTDH3, pPGK1, or pPYK1 as a promoter, and further includes a nutrition complementary gene (for example, the URA3 gene, HIS3 gene, LYS2 gene, or LEU2 gene). Examples of the expression inducing factor include galactose.

Also in a yeast expression system, a protease recognition sequence may be incorporated into an expression vector. In the same manner as in an *E. coli* expression system, the expression vector used in a yeast expression system is, for example, constructed by any of the following methods (a) to (c). Many expression vectors useful in a yeast expression system have been developed, and the expression vector of the present invention may be constructed using an existing expression vector.

(a) A method of inserting a sequence coding a target protein, to which the peptide tag of the present invention is linked, into a vector for yeast expression;

(b) a method of inserting a sequence coding the target protein by in-frame into the vector for yeast expression having a sequence coding the peptide tag of the present invention immediately after the initiation codon, downstream from the sequence; or (c) a method of inserting a sequence coding the peptide tag of the present invention immediately after the initiation codon of the vector for yeast expression holding the sequence coding the target protein.

The yeast as a host may be, for example, *Saccharomyces cerevisiae, Schizosaccharomyces pombe*, or *Pichia pastoris*. Transformation of the host, culture of the transformant (expression of the target protein), and collection of the target protein may use ordinary methods.

(2) Cell-Free Synthesis System

In one embodiment of the present invention, a target protein is expressed using a cell-free protein synthesis using *E. coli*-derived components. The cell-free protein synthesis system doesn't use living cells, but uses, for example, ribosome or a transfer-translation factor derived from living cells (or obtained by a genetic engineering method) for synthesizing a protein in vitro from a nucleic acid as a template. In a cell-free protein synthesis system, a cell extract obtained by purifying a crushed cell liquid as necessary is commonly used. The cell extract generally contains ribosome necessary for protein synthesis, various factors such as an initiation factor, and various enzymes such as tRNA. When protein synthesis is carried out, other substances necessary for protein synthesis, such as energy sources including various amino acids, ATP, and GTP, and creatine phosphate are added to the cell extract. At the time of the protein synthesis, ribosome, any factor, and/or any enzyme, which are provided additionally, may be as added as necessary.

There are some reports of the development of a transcription/translation system made by reconstructing the molecules (factors) necessary for protein synthesis (for example, Shimizu, Y. et al.: Nature Biotech., 19, 751-755, 2001). In this synthesis system, the genes of 31 factors composed of three initiation factors, three elongation factors, four factors involved in completion, 20 aminoacyl-tRNA synthases bonding amino acids to tRNA, and methionyl tRNA formyl transferase, which composes a bacterial protein synthesis system, are amplified from an *E. coli* genome, and a protein synthesis system is reconstructed in vitro using them. In the present invention, a reconstituted synthesis system of this kind may be used.

The cell-free protein synthesis system has the following advantages. Firstly, it doesn't require maintenance of living cells, and thus provides good operability and a high degree of freedom of the system. This allows designing of a synthesis system which is corrected or modified in various way according to the properties of the desired protein. Secondly, when a cell system is used for synthesis, it is basically impossible to synthesize a protein toxic to the cells, but a cell-free system can produce such a toxic protein. Furthermore, many kinds of proteins can be synthesized simultaneously and rapidly, which facilitates high-throughput. This system also has advantages that the protein produced is readily separated and purified, which is advantageous to the increase of throughput. In addition to this, this system can synthesize a non-natural protein by, for example, incorporating a non-natural amino acid.

In the present invention, a system based on an *E. coli* S30 extract (a procaryotic cell system), or the above-described reconstructed system based on an *E. coli* genome. These systems are commercially available in the form of a kit, and can be used easily.

As a cell-free protein synthesis system, for example a system of a wheat germ extract (an eucaryotic cell system) and a system of rabbit solubilized reticulocytes (an eucaryotic cell system) are known. Historically, the system of an *E. coli* S30 extract is the oldest, and synthesis of various proteins has been attempted using this system. The *E. coli* S30 fraction is prepared through the steps of collection of *E. coli*, crashing of bacterial cells, and purification. The preparation of the *E. coli* S30 fraction and the cell-free transfer-translation coupled reaction may be carried with reference to the method by Pratt et al. (Pratt, J. M.: Chapter 7, in "Transcription and Translation: A practical approach", ed. by B. D. Hames & S. J. Higgins, pp. 179-209, IRL Press, New York (1984)), and the method by Ellman et al. (Ellman, J. et al.: Methods Enzymol., 202, 301-336 (1991)).

Also when a target protein is expressed using a cell-free protein synthesis system, an expression vector having the same composition as the above-described *E. coli* expression system can be used. However, the expression vector used in a cell-free protein synthesis system does not necessarily require the origin of replication. Additionally, in a cell-free protein synthesis system, the template for expressing a target protein is not limited to an expression vector in the form of a plasmid DNA, but may be a linear DNA (for example, that obtained by amplifying a part of the plasmid DNA (the part necessary for the expression of the target protein)), an mRNA (for example, that obtained by transferring the linear DNA), or a concatemer DNA (a DNA to which plural unit sequences are linked in series, which can be prepared by, for example, a rolling circle amplification method).

When a cell-free protein synthesis system is used, a template for expression containing the sequence coding the target protein to which the peptide tag of the present invention is linked at the N-terminal (for example, an expression vector, linear DNA, or mRNA) is provided (step (i)), and cell-free protein synthesis reaction is carried out (step (ii)). Collection of the target protein as the expression product may be carried out in the same manner as the *E. coli* expression system.

2. Expression Vector and Expression Kit

The expression vector used for the expression method of the present invention (especially those having a cloning site) provides marked versatility, and has high usefulness and utility value by itself. Therefore, as another aspect, the present invention provides an expression vector which can be used in the expression method of the present invention. The composition of the expression vector of the present invention is as described above, and includes the elements necessary for expression of a target protein in an *E. coli* expression system, a cell-free protein synthesis system using an *E. coli*-derived component, or a yeast expression system.

The present invention further provides a kit for expressing a target protein containing the expression vector of the present invention. This kit allows more simple production of a target protein using the expression method of the present invention. The kit of the present invention includes the above-described expression vector (for an expression system using an E. coli or a yeast expression system) as a main component. On the other hand, it may include a reagent which specifically recognizes a tag-added protein as an expression product. The kit including this reagent facilitates detection and purification of the expression product. An example of the reagent is an antibody which recognizes the peptide tag of the present invention linked to the N-terminal of a protein (anti-peptide tag antibody). This antibody may be a polyclonal antibody or monoclonal antibody. Alternatively, it may be in the form of a fragment of an antibody such as a Fab, Fab', F (ab')$_2$, scFv, or dsFv, antibody. When a labeled antibody is used, detection and determination can be performed using the label as an index. In addition, in order to facilitate the detection and purification of a tag-added protein, an antibody supported by an insoluble support or a magnetic material may be used. The shape of the insoluble support/magnetic material carrying the antibody is not particularly limited. The shape may be, for example, a plate or particles. Examples of the material of the insoluble support include resins such as a polystyrene resin, a polycarbonate resin, a silicon resin, and a nylon resin, and glass. On the other hand, examples of the material of the magnetic material include iron oxides such as ferrite and magnetite, chromic oxide, and cobalt. In addition, the anti-peptide tag antibody is useful per se as a tool for, for example, investigation and development, and provides a high utility value. Accordingly, the anti-peptide tag antibody may be provided singly, not as a component of a kit, or in combination with other element (for example, a reagent necessary for using the anti-peptide tag antibody).

Furthermore, the kit may include a peptide having the peptide tag of the present invention at the N-terminal (hereinafter referred to as "peptide reagent"). This peptide reagent is used for purification of a tag-added protein. For example, an expressed tag-added protein is bound to the above-described reagent (that specifically recognized the tag-added protein), and then the peptide reagent is competitively acted thereon, whereby the trapped tag-added protein is dissociated, and collected. The length of the peptide composing the peptide reagent and the entire sequence are not particularly limited as long as the peptide contains the peptide tag of the present invention, and is suitable for this use. However, in consideration of the intended use, the properties necessary for it, and the production cost, the peptide reagent is preferably a peptide composed of the sequence of the peptide tag of the present invention (for example, SK, SKI, or SKIK (SEQ ID NO. 3)). The kit of the present invention may include other reagents (for example, an inducing agent such as IPTG), a container and an instrument, and a culture medium necessary for performing the expression method of the present invention. The kit of the present invention usually includes an instruction manual.

3. Recombinant Protein

According to the expression method of the present invention, a recombinant protein having a characteristic structure, specifically, a recombinant protein to which the peptide tag of the present invention is linked at the N-terminal. This recombinant protein has an advantage that it allows detection and purification using the peptide tag of the present invention. Accordingly, it provides high usefulness per se. As described above, the protein to which the expression method of the present invention can be applied is not particularly limited, and various target proteins may be obtained as "recombinant proteins to which a peptide tag is linked". In addition, a protease recognition sequence may be incorporated between the peptide tag and the target protein sequence, thereby cleaving (separating) the peptide tag portion by the action of protease, for example, after purification treatment or after fraction or fractionation.

EXAMPLES

1. Expression of Mouse Antibody

An antibody gene of anti-E. coli 0157 obtained from a mouse was expressed as Fab. The LZA (leucine zipper peptide A)-HA tag and the LZB (leucine zipper peptide B)-Flag tag were linked to the C-terminals of He and Lc, respectively. The leucine zipper peptide A and the leucine zipper peptide B have high affinity, and form a leucine zipper hetero dimer. The leucine zipper peptide A contains leucine in every seven residues, thereby forming a leucine zipper. The leucine zipper peptide B also contains leucine in every seven residues in the same manner. These leucines are placed so as to correspond to the leucine in the leucine zipper peptide A (that composing a leucine zipper motif).

Firstly, a heavy chain and light chain of the mouse antibody cloned from a hybridoma were amplified by the DNA primer pair TTAAGAAGGAGATATACATATG-GAGGTCCAGCTGCAACAGTCC (SEQ ID NO. 6) and GAGCTGGGCGCTCCCACCACCGCCTG-GAATGGGCACATGCAGATCTTTG (SEQ ID NO. 7), and the pair TAATAATCTAGAAGGAGATATCATATG-GATGTTTTGATGACCCAAAC (SEQ ID NO. 8) and CTGGGCGCTCCCACCACCGC-CACACTCTTTCCTGTTGAAGCTC (SEQ ID NO. 9), respectively. Additionally, the gene sequences of LZA and LZB were artificially synthesized by contract service of Lifetechnologies, and used as templates and amplified by the primer pairs of GGCGGTGGTGG-GAGCGCCCAGCTCGAAAAGGAG (SEQ ID NO. 10) and TGATATCTCCTTCTAGATTATTAAGCGTAATCTG-GAACATC (SEQ ID NO. 11), and the pair GGCGGTGGTGGGAGCGCCCAGCTCAAGAAGAAGC (SEQ ID NO. 12) and TCGTCGTCCTTGTAGTCG-GAACCGCCCTTC (SEQ ID NO. 13), respectively. Subsequently, the expression vector pET22b (Novagen), which had been linearized by CCGACTACAAGGACGAC-GATGACAAATAATAAGATCCGGCTGCTAACAAAGC (SEQ ID NO. 14) and CATATGTATATCTCCTTCTTAA (SEQ ID NO. 15), and the above-described four fragments were linked by Gibson assembly, thereby constructing an Fab expression plasmid wherein the heavy chain-LZA-HA tag and the light chain-LZB-Flag tag were linked via a short DNA containing RBS in the NdeI site sequence downstream of the T7 promoter. The DH5 alpha was transformed, and a plasmid was prepared from a transformant grown on an LB agar plate containing 100 µg/mL ampicillin. This was used as pET22b-m6FabLZ.

Using the pET22b-m6FabLZ as a template, the SKIK sequence 5'-tctaaaataaaa-3' (SEQ ID NO. 4) was inserted by PCR into He and Lc immediately after the initiation codon. More specifically, PCR was performed using the pair of aggagatatacatatgtctaaaataaaagaggtccagctg (SEQ ID NO. 16) and GTCATCAAAACATCTTTTATTTTAGACATATGA-TATCTCCTTCT (SEQ ID NO. 17), and the pair of taaaataaaagatgttttgatgacccaaac (SEQ ID NO. 18) and TAGACATATGTATATCTCCTTCT (SEQ ID NO. 19). KOD plus was used as a DNA polymerase. The temperature program was as follows: hold at 94° C. for 2 minutes, 25 cycles of 94° C. for 30 seconds, 55° C. for 30 seconds and 72° C. for 4 minutes, hold at 72° C. for 3 minutes. The PCR product thus obtained was purified, and linked to form a circle by Gibson assembly in the same manner as above. DH5 alpha was transformed, and a plasmid was prepared from a transformant grown on an LB agar plate containing 100 μg/mL ampicillin. This plasmid was used as pET22b-m6Fab-SKIK.

The expression used a Shuffle T7 express strain (NEB), and this strain was transformed by the above-described plasmid. The subsequent operation used a culture medium containing 100 μg/mL ampicillin. The single colony of the transformant thus obtained was seeded in 2 mL of LB culture medium, and cultured under shaking overnight at 37° C. This culture was seeded in 20 mL of Terrific broth, and cultured under shaking at 37° C. until the OD600 became 0.4 to 0.5. After that, the culture was rapidly cooled to 16° C., and cultured under shaking for 24 hours at 16° C. in the presence of 0.1 mM IPTG, thereby inducing the expression of the target gene. The cell pellets collected by centrifugation were suspended in 2 mL of PBS, and crushed by a bead crusher. Furthermore, they were centrifuged at 15000 rpm for 5 minutes, and the supernatant was used as a soluble fraction, the precipitate was used as an insoluble fraction, and the cell suspension was used as the whole cell fraction. They were analyzed by SDS-PAGE. The gel was stained by CBB.

Figure 1:
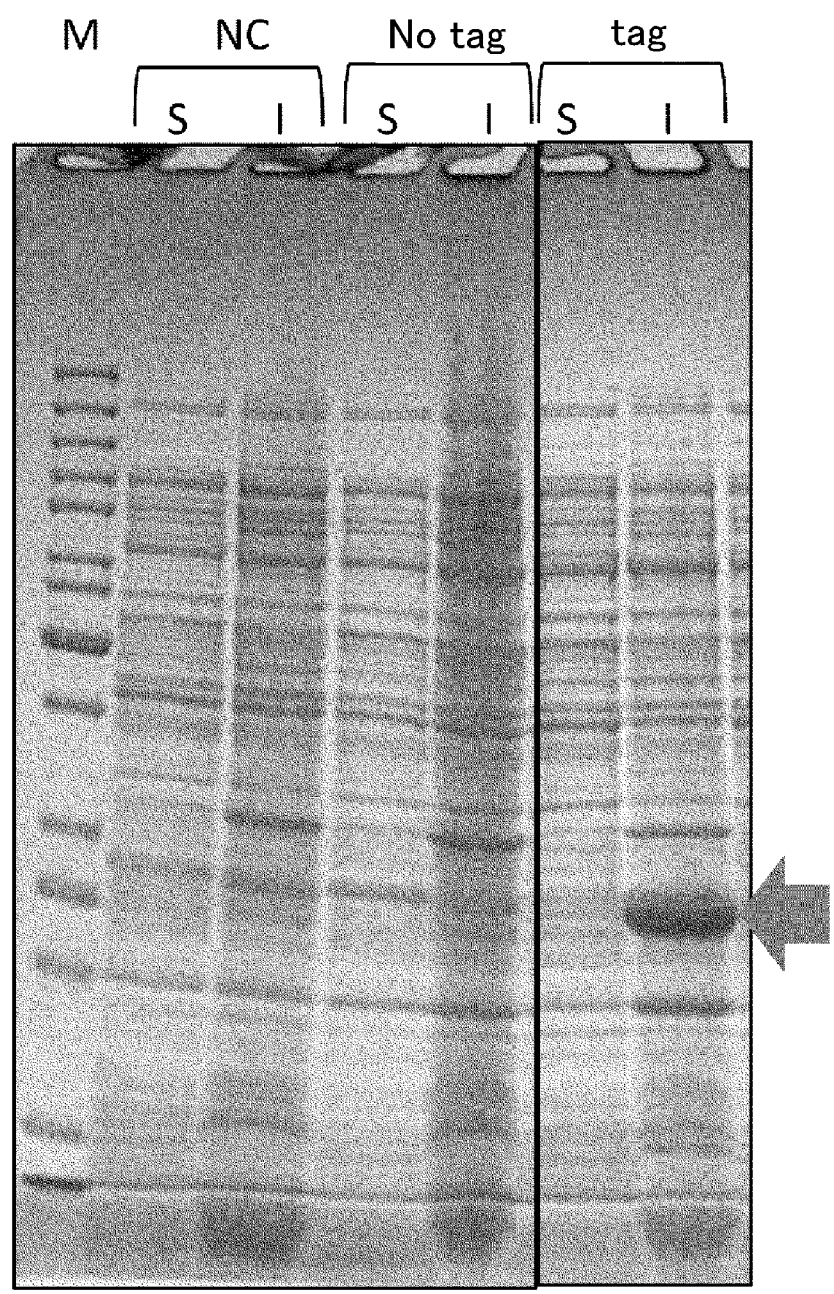
FIG. 1 shows the effect of the SKIK tag (SEQ ID NO. 3) on a mouse antibody. S: soluble fraction, I: insoluble fraction.

The result is shown in FIG. 1. The comparison of the insoluble fractions with and without tag indicates that the expression level was markedly higher for that with a tag.

2. Rabbit Antibody

The antibody genes No. 1, 4, and 9 of anti-*Listeria monocytogenes* obtained from a rabbit were expressed as scFv. The operation method and the treatment conditions followed the above-described experiment.

Figure 2:
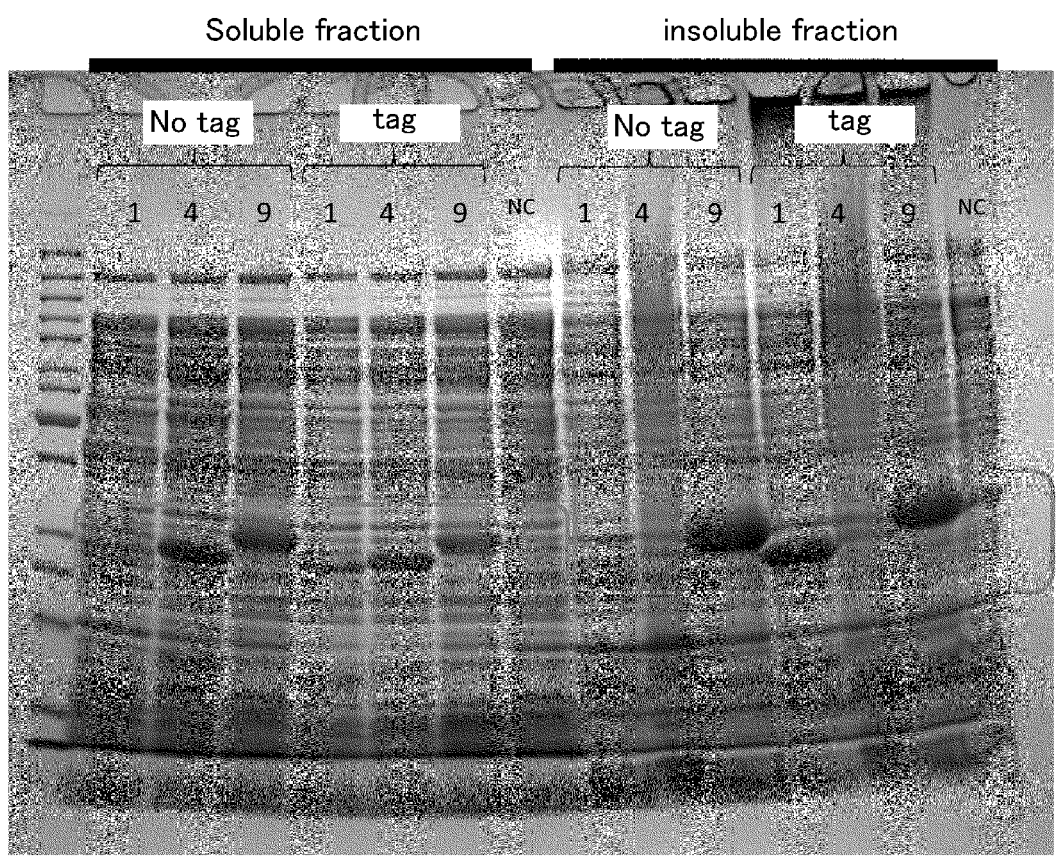
FIG. 2 shows the effect of the SKIK tag (SEQ ID NO. 3) on a rabbit antibody. Three kinds of rabbit antibodies (No. 1, 4, and 9) were expressed.

The result is shown in FIG. 2. No. 4 and 9 had intrinsically high expression levels, and their expression levels in the soluble fractions were still high regardless of the addition of a tag. On the other hand, for No. 1, the protein bands in the soluble and insoluble fractions became markedly thick by the addition of a tag, indicating the increase of expression level.

3. Expression of Artificial Peptide

A sequence coding the leucine zipper B was expressed, and the effect of increasing the expression level by tag addition was studied. The expression was carried out under the same operation and conditions as the above-described experiment, except that the induction and expression were carried out at 37° C. for 3 hours.

Figure 3:
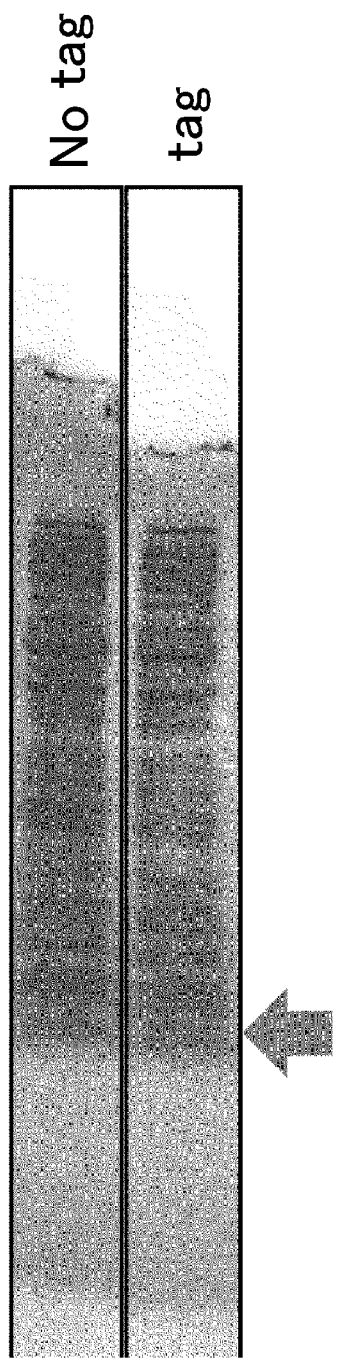
FIG. 3 shows the effect of the SKIK tag (SEQ ID NO. 3) on an artificial peptide.

The result is shown in FIG. 3. A protein band (represented by an arrow) was recognized only when a tag was added.

4. Comparison with Other Tag (T7 Tag)

The effect of the T7 tag sequence 5'-atggctagcatgactggtggacagcaaatgggt-3': SEQ ID NO. 20 (amino acid sequence MASMTGGQQMG: SEQ ID NO. 21), which is derived from the reader sequence of a bacteriophage capsid protein was compared with SKIK (SEQ ID NO. 3). As models, three kinds of rabbit-derived scFv (No. 1, 4, and 9) were used. The expression was carried out by *E. coli* Shuffle T7 express. SDS-PAGE was carried out using the crashed expression product as a sample, and the protein expression conditions were compared. In addition, the binding activity for the purified scFv antigen was evaluated by ELISA. In ELISA, the activity per unit protein amount was calculated.

The result of SDS-PAGE shows that the addition of the T7 tag and SKIK (SEQ ID NO. 3) increased the expression level of a protein whose expression level was originally small (FIG. 4, No. 1). On the other hand, when the T7 tag was added to those having high expression levels without a tag such as No. 4 and No. 9, a slight decrease was observed (FIG. 4, No. 4 and 9). These results show that SKIK (SEQ ID NO. 3) increases the expression level regardless the kind of protein, and will not give negative effect unlike the T7 tag.

The evaluation by ELISA showed that the T7 tag-added scFv of No. 4 had lost original binding activity (FIG. 5). The SKIK-added scFv showed similar binding activity to the tag-free scFv (original antibody). The reason for this is likely that SKIK (SEQ ID NO. 3) is greatly shorter than the T7 tag, so that it has limited influence on the function of the antibody itself.

5. Influence of Codon

The codon influence relating to the effect of SKIK (SEQ ID NO. 3) was studied. The sequence coding the above-described SKIK (5'-tctaaaataaaa-3': SEQ ID NO. 4) was compared with the sequence including a different codon (5'-tcgaagatcaag-3': SEQ ID NO. 5; the peptide coded by the sequence is referred to as "SKIK2" for convenience). The No. 1 gene of rabbit scFv was used as a model, expressed in the same manner as in the above-described experiment, and subjected to CBB staining after SDS-PAGE, thereby comparing the expression levels (FIG. 6). The expression level of the target protein was increased by both of these base sequences, so that achievement of the desired effect (the increase in the expression level of the target protein) is expected regardless of the type of the codon as long as it codes SKIK (SEQ ID NO. 3).

6. Validation of Tag Effect in Cell-Free Synthesis System

The effect of the SKIK tag (SEQ ID NO. 3) sequence by a cell-free protein synthesis system of *E. coli* was studied. The rabbit anti-*Listeria* scFv was used as a model. The pET22b-r1scFv-HA and pET22b-SKIK-r1scFv-HA were used as templates, and amplified by the primer pair of atctcgatcccgcgaaattaatacg (SEQ ID NO. 22) and tccggatatagttcctccttttcag (SEQ ID NO. 23), thus obtaining DNA fragments for expression containing the T7 promoter and terminator upstream and downstream of the target gene, respectively. In the same manner, a fragment for expressing fluorescent protein GFP as a positive control was also amplified by PCR. The PCR product of about 1 kb thus obtained was subjected to column purification, and adjusted to a DNA concentration of 60 to 65 ng/.mu.L. This was used as a template for a cell-free protein synthesis system. For a negative control, a TE buffer solution was added in place of a template DNA.

The reaction composition of the cell-free protein synthesis is as shown in Table 1 (cell-free protein synthesis reaction composition) and Table 2 (LM composition). After hot water bathing at 30° C. for 60 minutes for reaction, 1 μL of 1 mg/mL RNase was added to remove RNA. The whole fraction of the reaction liquid itself was centrifuged at 13000 rpm for 10 minutes, and the supernatant and precipitate were used as soluble and insoluble fractions, respectively. Reduction treatment was performed by 2-mercaptoethanol, the volumes of the fractions were equalized, and subjected to SDS-PAGE (gel concentration: 12.5%). The detection used Tyhoon.

TABLE 1

|  | Amount (μL) |
| --- | --- |
| 5M KOAc | 0.6 |
| 0.2M Mg(OAc)2 | 0.9 |
| 0.1 mg/mL rifampicin | 3 |
| LM | 7.5 |
| 10 mg/mL creatine kinase | 0.45 |

TABLE 1-continued

| | Amount (μL) |
|---|---|
| 100 mM GSSG | 0.6 |
| S30 extract of *E. coli* (BL21 Star (DE3) pSJS1240 | 8.5 |
| 10 mM GSH | 1 |
| DNA template (60 ng/μL) | 1 |
| Water | 6.15 |
| Fluorescence-labeled lysine | 0.3 |
| Total | 30 |

TABLE 2

| | Concentration | |
|---|---|---|
| Tris-acetate buffer (pH 7.4) | 220 | mM |
| ATP | 2.4 | mM |
| GTP CTP UTP mix | 4 | mM |
| Disodium creatinephosphate | 240 | mM |
| 20 amino acids | 8.4 | mM |
| Folinic acid | 512 | μg/mL |
| Ammonium acetate | 143.2 | mM |
| *E. coli* tRNA | 680 | μg/mL |

The result is shown in FIG. 7. For the tag-free scFv, no protein band was found in all the fractions. On the other hand, for the SKIK tag (SEQ ID NO. 3)-added one, a clear band was found, indicating that the expression level in the system was greatly increased (an arrow in FIG. 7). This result shows that the SKIK tag (SEQ ID NO. 3) increases the expression level of a target protein not only in an in vivo system but also in an in vitro system of *E. coli*.

7. Influence of Control Promoter

In order to study the influence by the type of the promoter (promoter dependence), the expression level under T7 promoter control was compared with that under cold shock promoter cspA control. The model gene was the anti-0157 mouse antibody which shows a low expression level when no SKIK tag (SEQ ID NO. 3) is added (referred to as m6FabLZ). This gene was cloned in frame with the initiation codon of pET22b (Novagen; T7 promoter control) and pColdI (Takara; cspA promoter control), and expressed by a Shuffle T7 express strain. The induction culture medium used Terrific Broth containing 100 μg/mL ampicillin. The induction was carried out at 16° C. for 24 hours in the presence of 1 mM IPTG. The bacterial cells was collected by centrifugation at 5000×g, and washed by PBS. The washed bacterial cells in the same amounts were suspended in a sample buffer containing a reducing agent, boiled for 5 minutes, and then subjected to SDS-PAGE (gel concentration: 12.5%). Protein bands were detected by CBB staining.

The result of SDS-PAGE on the bacterial cells in the same amounts under electrophoresis is shown in FIG. 8. The antibody fragment size indicated by an arrow could not be detected for the negative control (pET22b) and tag-free. On the other hand, in both of the promoters tested herein, the SKIK tag (SEQ ID NO. 3)-added one was detected as a main band. This indicated that the expression level was increased by the SKIK tag (SEQ ID NO. 3). From this result, it is expected that the SKIK tag (SEQ ID NO. 3) will achieve its effect under control of any promoter in *E. coli*.

8. Study of Tag Length

In order to study the influence of the reduction of the tag length, a comparison was made between the five series: those composed of a tag sequence (sequence coding S, SK, SKI, or SKIK (SEQ ID NO. 3)) between the initiation codon and anti-*Listeria*-rabbit antibody gene (referred to as r1scFv) (four series), and a tag-free one (one series). The vector was pET22b, and the PelB signal sequence was removed. The expression host was Shuffle T7 express in the same manner as above, and the induction culture medium was LB culture medium containing 100 μg/mL ampicillin. The induction was carried out at 16° C. for 24 hours in the presence of 1 mM IPTG. The bacterial cells was collected by centrifugation at 5000×g, and washed by PBS. The washed bacterial cells in the same amounts were suspended in a sample buffer containing a reducing agent, boiled for 5 minutes, and then subjected to SDS-PAGE (gel concentration: 12.5%). Protein bands were detected by CBB staining.

The result of SDS-PAGE on the bacterial cells in the same amounts under electrophoresis is shown in FIG. 9. The band level of the target protein increased in the order of tag-free<S<SK<SKI<SKIK tag (SEQ ID NO. 3), showing a marked increase for SKI and SKIK (SEQ ID NO. 3). This result indicates that the tag length for increasing the expression level is preferably two or more amino acids containing SK, and more preferably three to four amino acids containing SKI.

9. Effect in Yeast Expression System

The No. 4 rabbit scFv gene was used as a model and the low copy plasmid pYC2/NT was used as an expression vector. Firstly, the pYC2/NT was subjected to PCR and linearized by the primer pair of TTTTTTCGGTAC-CAAGCTTAATATTCCC (SEQ ID NO. 24) and TAACT-GATCCTAGAGGGCCGCATCATG (SEQ ID NO. 25). Secondly, using the *E. coli* expression plasmids into which the tag-free and SKIK tag (SEQ ID NO. 3)-added No. 4 scFv gene had been inserted were used as templates, amplification was carried out by the pair of TAAGCTTGGTACCGAAAAAAATGGATGTCGT-GATGACCCAGAC (SEQ ID NO. 26) and GGCCCTCTAGGATCAGTTAAGCGTAATCTGGAA-CATCGTATG (SEQ ID NO. 27), and the pair of (r4scFv-pYC-R) and TAAGCTTGGTACCGAAAAAAATGtctaaa-ataaaaGATGTCGTGATGACC (SEQ ID NO. 28) and r4scFv-pYC-R, respectively. Each of them was linked to the linearized pYC2/NT by Gibson assembly, thus constructing yeast expression plasmids.

A plasmid was prepared from a colony of transformed DH5alpha grown on an LB culture medium containing 100 μg/mL ampicillin. Competent cells of the yeast *S. cerevisiae* INVsc1 strain (Lifetechnologies) was transformed by this plasmid, and applied to a uracil-deficient synthetic agar media (SD-U culture medium, carbon source: 2% glucose). The transformant thus obtained was seeded in an SD-U liquid medium, and cultured overnight (preculture). A total of 100 μL of the preculture solution was subcultured in 3 mL of a new SD-U liquid medium, and cultured for 3 hours. After that, the bacterial cells were aseptically collected by centrifugation at 5000×G for 3 minutes, and washed twice by 1 mL portions of PBS. The culture medium was replaced with 3 mL of a uracil-deficient synthetic induction culture medium (SG-U, carbon source: 2% galactose and 1% raffinose), and subjected to expression induction for 24 hours. All the cultures were aerobically carried out at 30° C., 150 rpm.

The bacterial cells were collected in the same manner as described above, washed with PBS, and then suspended in 1 mL of PBS. A total of 900 μL of the suspension was placed in a bead crusher, and the cells were crushed. Then, soluble and insoluble fractions were obtained by centrifugation at 15000 rpm for 5 minutes. The remaining 100 μL was used as a whole cell fraction.

After the protein was isolated by reduction SDS-PAGE, and then transferred to a cellulose nitrate membrane. This was subjected to blocking treatment for 30 minutes by a SuperBlock™ (PBS) Blocking buffer. Thereafter, the membrane after blocking treatment was immersed in 10 mL of a liquid prepared by diluting an anti-HA tag antibody (Wako Pure Chemical Industries, Ltd., Anti HA, Monoclonal Antibody, Peroxidase Conjugated) with 500 times of the above-described blocking agent, and allowed to react under shaking for 90 minutes. Washing (10 minutes) by PBS containing 0.05% tween20 was repeated four times, and then 1 mL of 1 step Ultra TMB blotting solution (Thermo) was dropped on the membrane, thereby visualizing the HA tag added No. 4 scFv. As a result of this, a thicker band was found in the tag-added fraction in comparison with the tag-free fraction (FIG. 10).

10. Study of Other Tag

Using, as a model, the rabbit scFv whose expression level is low without using the tag, the effect of the peptide tag other than SKIK (SEQ ID NO. 3) was studied. First, using the pET22b-r1scFv-HA as a template, PCR was performed by the primers atatgaaaaaaaaaaaagaccctatgctgacc (SEQ ID NO. 41) and AGGGTCTTTTTTTTTTTT-CATATGTATATCTCC (SEQ ID NO. 42), and KKKK (SEQ ID NO. 35) (aaaaaaaaaaaa (SEQ ID NO. 40) was used as a base sequence) was added to the N-terminal. In the same manner, AKIK (SEQ ID NO. 33) (gcaaaaattaaa (SEQ ID NO. 38) was used as a base sequence) was added by atatggcaaaaattaaagaccctatgctgacc (SEQ ID NO. 43) and AGGGTCTTTAATTTTTGCCATATGTATATCTCC (SEQ ID NO. 44), SKKK (SEQ ID NO. 32) (tctaaaaaaaaa (SEQ ID NO. 37) was used as a base sequence) was added by atatgtctaaaaaaaaagaccctatgctgacc (SEQ ID NO. 45) and AGGGTCTTTTTTTTTAGACATATGTATATCTCC (SEQ ID NO. 46), AKII (SEQ ID NO. 34) (gcaaaaattatt (SEQ ID NO. 39) was used as a base sequence) by atatggcaaaaattattgaccctatgctgacc (SEQ ID NO. 47) and AGGGTCAATAAT-TTTTGCCATATGTATATCTCC (SEQ ID NO. 48), and SKIT (SEQ ID NO. 31) (tctaaaattatt (SEQ ID NO. 36) was used as a base sequence) was added by atatgtctaaaattatt-gaccctatgctgacc (SEQ ID NO. 49) and AGGGTCAATAAT-TTTAGACATATGTATATCTCC (SEQ ID NO. 50). Using these tags, the target proteins were expressed in the cells of *E. coli* in the same manner as in the above-described Example 1 (expression of a mouse antibody). In this experiment, an LB culture medium was used for expression. The whole cell fractions thus obtained were separated by SDS-PAGE, and stained by CBB. The result is shown in FIG. 12. From this result, it was found that SKXX (SEQ ID NO. 1), AKXX (SEQ ID NO. 29), and KKXX (SEQ ID NO. 30) also have the effect of increasing the expression level.

INDUSTRIAL APPLICABILITY

According to the expression method of the present invention, the expression level of a target protein can be increased by simple operations. In the expression method of the present invention, a target protein to which a peptide tag is linked is expressed. The peptide tag used herein is short, and its possibility to affect the activity of the target protein is extremely low. Accordingly, the present invention is especially useful as a means for expressing biologically active proteins such as enzymes and antibodies in large amounts. In addition, the present invention provides marked versatility, and is expected to be used for the expression of various proteins.

The present invention is not limited to the above-described embodiments and the explanation of examples of the present invention. Various modifications which can be readily conceived by those skilled in the art are included in the invention, without departing from the scope of the invention. The entire contents of the literatures, unexamined patent publications, and patent publications cited herein are incorporated herein by reference.

SEQUENCE LIST FREE TEXT

SEQ ID NO. 1 to 5, 29 to 40: explanation of artificial sequence: tag sequence
SEQ ID NO. 6 to 19, 22 to 28, and 41 to 50: explanation of artificial sequence: primer
SEQ ID NO. 20, 21: explanation of artificial sequence: T7 tag

---

The invention claimed is:

1. A protein expression method comprising expressing a target protein as a tag-added protein to which a peptide tag composed of an amino acid sequence SK, SKX, SEQ ID NO. 1, SEQ ID NO. 29, or SEQ ID NO. 30 is linked at the N-terminal by an *E. coli* expression system or a yeast expression system.

2. The expression method of claim 1, wherein the peptide tag is composed of an amino acid sequence SKI, SEQ ID NO. 3, SEQ ID NO. 32, SEQ ID NO. 31, SEQ ID NO. 33, SEQ ID NO. 34, or SEQ ID NO. 35.

3. The expression method of claim 1, wherein the peptide tag and the sequence of the target protein are directly linked together.

4. The expression method of claim 1, wherein a protease recognition sequence is sandwiched between the peptide tag and the target protein sequence.

5. The expression method of claim 1, wherein the *E. coli* expression system is an expression system using a T7 promoter or a low temperature expressing promoter.

6. The expression method of claim 1, which comprises the following steps (1) to (3):

(1) a step of providing an expression vector comprising a sequence coding a target protein to which the peptide tag is linked at the N-terminal;

(2) a step of introducing the expression vector into a host cell; and (3) a step of culturing a transformant into which the expression vector has been introduced, thereby expressing the target protein.

7. The expression method of claim 6, wherein the expression vector is constructed by any of the following methods (a) to (c):
   (a) inserting a sequence coding a target protein, to which a peptide tag is linked, into the vector for expressing the host cell,
   (b) inserting a sequence coding a target protein in-frame into a vector for expressing the host cell having a sequence coding the peptide tag immediately after the initiation codon, downstream from the sequence,
   (c) inserting a sequence coding a peptide tag immediately after the initiation codon of the vector for expressing the host cell holding the sequence coding the target protein.

8. The expression method of claim 1, wherein the *E. coli* expression system is a cell-free protein synthesis system using an *E. coli*-derived component.

9. The expression method of claim 8, which comprises the following steps (i) and (ii):
   (i) providing a template for expression containing a sequence coding the target protein to which the peptide tag is linked at the N-terminal; and
   (ii) conducting a cell-free protein synthesis.

10. An expression vector for an *E. coli* expression system, comprising:
    a promoter functional in *E. coli*;
    a ribosome binding site;
    an initiation codon;
    a sequence coding a peptide tag composed of an amino acid sequence SK, SKX, SEQ ID NO. 1, SEQ ID NO. 29, or SEQ ID NO. 30, which is placed immediately after the initiation codon; and
    a cloning site placed downstream of the sequence.

11. The expression vector of claim 10, wherein the sequence coding a peptide tag and the cloning site are adjacent to each other.

12. The expression vector of claim 10, wherein a sequence coding a protease recognition sequence is placed between the sequence coding a peptide tag and the cloning site.

13. A kit for expressing a target protein, comprising the expression vector of claim 10.

14. The kit of claim 13, which further comprises an antibody recognizing the peptide tag linked to the N-terminal of a protein.

15. The kit of claim 14, wherein the antibody is supported by an insoluble support or a magnetic material.

16. The kit of claim 13, which further comprises a peptide having the peptide tag at the N-terminal.

17. An expression vector for a yeast expression system, comprising:
    a promoter functional in a yeast;
    an initiation codon;
    a sequence coding a peptide tag composed of an amino acid sequence SK, SKX, SEQ ID NO. 1, SEQ ID NO. 29, or SEQ ID NO. 30, which is placed immediately after the initiation codon; and
    a cloning site placed downstream of the sequence.

18. An expression vector for an *E. coli* expression system, comprising:
    a promoter functional in *E. coli*;
    a ribosome binding site;
    an initiation codon;
    a sequence coding a peptide tag composed of an amino acid sequence SK, SKX, SEQ ID NO. 1, SEQ ID NO. 29, or SEQ ID NO. 30, which is placed immediately after the initiation codon; and
    a sequence coding a target protein placed downstream of the sequence.

19. An expression vector for a yeast expression system, comprising:
    a promoter functional in a yeast;
    an initiation codon;
    a sequence coding a peptide tag composed of an amino acid sequence SK, SKX, SEQ ID NO. 1, SEQ ID NO. 29, or SEQ ID NO. 30, which is placed immediately after the initiation codon; and
    a sequence coding a target protein placed downstream of the sequence.

20. A recombinant protein to which a peptide tag composed of an amino acid sequence SK, SKX, SEQ ID NO. 1, SEQ ID NO. 29, or SEQ ID NO. 30 is linked at the N-terminal.

* * * * *

SEQUENCE LISTING

```
<160> NUMBER OF SEQ ID NOS: 50

<210> SEQ ID NO 1
<211> LENGTH: 4
<212> TYPE: PRT
<213> ORGANISM: Artificial Sequence
<220> FEATURE:
<223> OTHER INFORMATION: tag sequence
<220> FEATURE:
<221> NAME/KEY: MISC_FEATURE
<222> LOCATION: (3)..(3)
<223> OTHER INFORMATION: any amino acid
<220> FEATURE:
<221> NAME/KEY: MISC_FEATURE
<222> LOCATION: (4)..(4)
<223> OTHER INFORMATION: any amino acid

<400> SEQUENCE: 1

Ser Lys Xaa Xaa
1

<210> SEQ ID NO 2
<211> LENGTH: 4
```

```
<212> TYPE: PRT
<213> ORGANISM: Artificial Sequence
<220> FEATURE:
<223> OTHER INFORMATION: tag sequence
<220> FEATURE:
<221> NAME/KEY: MISC_FEATURE
<222> LOCATION: (4)..(4)
<223> OTHER INFORMATION: any amino acid

<400> SEQUENCE: 2

Ser Lys Ile Xaa
1

<210> SEQ ID NO 3
<211> LENGTH: 4
<212> TYPE: PRT
<213> ORGANISM: Artificial Sequence
<220> FEATURE:
<223> OTHER INFORMATION: tag sequence

<400> SEQUENCE: 3

Ser Lys Ile Lys
1

<210> SEQ ID NO 4
<211> LENGTH: 12
<212> TYPE: DNA
<213> ORGANISM: Artificial Sequence
<220> FEATURE:
<223> OTHER INFORMATION: tag sequence

<400> SEQUENCE: 4
tctaaaataa aa                                                          12

<210> SEQ ID NO 5
<211> LENGTH: 12
<212> TYPE: DNA
<213> ORGANISM: Artificial Sequence
<220> FEATURE:
<223> OTHER INFORMATION: tag sequence

<400> SEQUENCE: 5
tcgaagatca ag                                                          12

<210> SEQ ID NO 6
<211> LENGTH: 43
<212> TYPE: DNA
<213> ORGANISM: Artificial Sequence
<220> FEATURE:
<223> OTHER INFORMATION: primer

<400> SEQUENCE: 6
ttaagaagga gatatacata tggaggtcca gctgcaacag tcc                        43

<210> SEQ ID NO 7
<211> LENGTH: 49
<212> TYPE: DNA
<213> ORGANISM: Artificial Sequence
<220> FEATURE:
<223> OTHER INFORMATION: primer

<400> SEQUENCE: 7
gagctgggcg ctcccaccac cgcctggaat gggcacatgc agatctttg                  49

<210> SEQ ID NO 8
<211> LENGTH: 47
<212> TYPE: DNA
```

```
<213> ORGANISM: Artificial Sequence
<220> FEATURE:
<223> OTHER INFORMATION: primer

<400> SEQUENCE: 8
taataatcta gaaggagata tcatatggat gttttgatga cccaaac                    47

<210> SEQ ID NO 9
<211> LENGTH: 43
<212> TYPE: DNA
<213> ORGANISM: Artificial Sequence
<220> FEATURE:
<223> OTHER INFORMATION: primer

<400> SEQUENCE: 9
ctgggcgctc ccaccaccgc cacactcttt cctgttgaag ctc                       43

<210> SEQ ID NO 10
<211> LENGTH: 33
<212> TYPE: DNA
<213> ORGANISM: Artificial Sequence
<220> FEATURE:
<223> OTHER INFORMATION: primer

<400> SEQUENCE: 10
ggcggtggtg ggagcgccca gctcgaaaag gag                                  33

<210> SEQ ID NO 11
<211> LENGTH: 41
<212> TYPE: DNA
<213> ORGANISM: Artificial Sequence
<220> FEATURE:
<223> OTHER INFORMATION: primer

<400> SEQUENCE: 11
tgatatctcc ttctagatta ttaagcgtaa tctggaacat c                         41

<210> SEQ ID NO 12
<211> LENGTH: 34
<212> TYPE: DNA
<213> ORGANISM: Artificial Sequence
<220> FEATURE:
<223> OTHER INFORMATION: primer

<400> SEQUENCE: 12
ggcggtggtg ggagcgccca gctcaagaag aagc                                 34

<210> SEQ ID NO 13
<211> LENGTH: 30
<212> TYPE: DNA
<213> ORGANISM: Artificial Sequence
<220> FEATURE:
<223> OTHER INFORMATION: primer

<400> SEQUENCE: 13
tcgtcgtcct tgtagtcgga accgcccttc                                      30

<210> SEQ ID NO 14
<211> LENGTH: 52
<212> TYPE: DNA
<213> ORGANISM: Artificial Sequence
<220> FEATURE:
<223> OTHER INFORMATION: primer

<400> SEQUENCE: 14
ccgactacaa ggacgacgat gacaaataat aagatccggc tgctaacaaa gc             52
```

```
<210> SEQ ID NO 15
<211> LENGTH: 22
<212> TYPE: DNA
<213> ORGANISM: Artificial Sequence
<220> FEATURE:
<223> OTHER INFORMATION: primer

<400> SEQUENCE: 15
catatgtata tctccttctt aa                                              22

<210> SEQ ID NO 16
<211> LENGTH: 40
<212> TYPE: DNA
<213> ORGANISM: Artificial Sequence
<220> FEATURE:
<223> OTHER INFORMATION: primer

<400> SEQUENCE: 16
aggagatata catatgtcta aaataaaaga ggtccagctg                           40

<210> SEQ ID NO 17
<211> LENGTH: 44
<212> TYPE: DNA
<213> ORGANISM: Artificial Sequence
<220> FEATURE:
<223> OTHER INFORMATION: primer

<400> SEQUENCE: 17
gtcatcaaaa catcttttat tttagacata tgatatctcc ttct                      44

<210> SEQ ID NO 18
<211> LENGTH: 30
<212> TYPE: DNA
<213> ORGANISM: Artificial Sequence
<220> FEATURE:
<223> OTHER INFORMATION: primer

<400> SEQUENCE: 18
taaaataaaa gatgttttga tgacccaaac                                      30

<210> SEQ ID NO 19
<211> LENGTH: 23
<212> TYPE: DNA
<213> ORGANISM: Artificial Sequence
<220> FEATURE:
<223> OTHER INFORMATION: primer

<400> SEQUENCE: 19
tagacatatg tatatctcct tct                                             23

<210> SEQ ID NO 20
<211> LENGTH: 33
<212> TYPE: DNA
<213> ORGANISM: Artificial Sequence
<220> FEATURE:
<223> OTHER INFORMATION: T7 tag

<400> SEQUENCE: 20
atggctagca tgactggtgg acagcaaatg ggt                                  33

<210> SEQ ID NO 21
<211> LENGTH: 11
<212> TYPE: PRT
<213> ORGANISM: Artificial Sequence
<220> FEATURE:
```

<223> OTHER INFORMATION: T7 tag

<400> SEQUENCE: 21

Met Ala Ser Met Thr Gly Gly Gln Gln Met Gly
1               5                   10

<210> SEQ ID NO 22
<211> LENGTH: 25
<212> TYPE: DNA
<213> ORGANISM: Artificial Sequence
<220> FEATURE:
<223> OTHER INFORMATION: primer

<400> SEQUENCE: 22
atctcgatcc cgcgaaatta atacg                                             25

<210> SEQ ID NO 23
<211> LENGTH: 24
<212> TYPE: DNA
<213> ORGANISM: Artificial Sequence
<220> FEATURE:
<223> OTHER INFORMATION: primer

<400> SEQUENCE: 23
tccggatata gttcctcctt tcag                                              24

<210> SEQ ID NO 24
<211> LENGTH: 28
<212> TYPE: DNA
<213> ORGANISM: Artificial Sequence
<220> FEATURE:
<223> OTHER INFORMATION: primer

<400> SEQUENCE: 24 tttttcggt accaagctta atattccc                                           28

<210> SEQ ID NO 25
<211> LENGTH: 27
<212> TYPE: DNA
<213> ORGANISM: Artificial Sequence
<220> FEATURE:
<223> OTHER INFORMATION: primer

<400> SEQUENCE: 25
taactgatcc tagagggccg catcatg                                           27

<210> SEQ ID NO 26
<211> LENGTH: 43
<212> TYPE: DNA
<213> ORGANISM: Artificial Sequence
<220> FEATURE:
<223> OTHER INFORMATION: primer

<400> SEQUENCE: 26
taagcttggt accgaaaaaa atggatgtcg tgatgaccca gac                         43

<210> SEQ ID NO 27
<211> LENGTH: 42
<212> TYPE: DNA
<213> ORGANISM: Artificial Sequence
<220> FEATURE:
<223> OTHER INFORMATION: primer

<400> SEQUENCE: 27
ggccctctag gatcagttaa gcgtaatctg gaacatcgta tg                          42

```
<210> SEQ ID NO 28
<211> LENGTH: 50
<212> TYPE: DNA
<213> ORGANISM: Artificial Sequence
<220> FEATURE:
<223> OTHER INFORMATION: primer

<400> SEQUENCE: 28
taagcttggt accgaaaaaa atgtctaaaa taaaagatgt cgtgatgacc            50

<210> SEQ ID NO 29
<211> LENGTH: 4
<212> TYPE: PRT
<213> ORGANISM: Artificial Sequence
<220> FEATURE:
<223> OTHER INFORMATION: tag sequence
<220> FEATURE:
<221> NAME/KEY: MISC_FEATURE
<222> LOCATION: (3)..(3)
<223> OTHER INFORMATION: any amino acid
<220> FEATURE:
<221> NAME/KEY: MISC_FEATURE
<222> LOCATION: (4)..(4)
<223> OTHER INFORMATION: any amino acid

<400> SEQUENCE: 29

Ala Lys Xaa Xaa
1

<210> SEQ ID NO 30
<211> LENGTH: 4
<212> TYPE: PRT
<213> ORGANISM: Artificial Sequence
<220> FEATURE:
<223> OTHER INFORMATION: tag sequence
<220> FEATURE:
<221> NAME/KEY: MISC_FEATURE
<222> LOCATION: (3)..(3)
<223> OTHER INFORMATION: any amino acid
<220> FEATURE:
<221> NAME/KEY: MISC_FEATURE
<222> LOCATION: (4)..(4)
<223> OTHER INFORMATION: any amino acid

<400> SEQUENCE: 30

Lys Lys Xaa Xaa
1

<210> SEQ ID NO 31
<211> LENGTH: 4
<212> TYPE: PRT
<213> ORGANISM: Artificial Sequence
<220> FEATURE:
<223> OTHER INFORMATION: tag sequence

<400> SEQUENCE: 31

Ser Lys Ile Ile
1

<210> SEQ ID NO 32
<211> LENGTH: 4
<212> TYPE: PRT
<213> ORGANISM: Artificial Sequence
<220> FEATURE:
<223> OTHER INFORMATION: tag sequence

<400> SEQUENCE: 32

Ser Lys Lys Lys
1
```

<210> SEQ ID NO 33
<211> LENGTH: 4
<212> TYPE: PRT
<213> ORGANISM: Artificial Sequence
<220> FEATURE:
<223> OTHER INFORMATION: tag sequence

<400> SEQUENCE: 33

Ala Lys Ile Lys
1

<210> SEQ ID NO 34
<211> LENGTH: 4
<212> TYPE: PRT
<213> ORGANISM: Artificial Sequence
<220> FEATURE:
<223> OTHER INFORMATION: tag sequence

<400> SEQUENCE: 34

Ala Lys Ile Ile
1

<210> SEQ ID NO 35
<211> LENGTH: 4
<212> TYPE: PRT
<213> ORGANISM: Artificial Sequence
<220> FEATURE:
<223> OTHER INFORMATION: tag sequence

<400> SEQUENCE: 35

Lys Lys Lys Lys
1

<210> SEQ ID NO 36
<211> LENGTH: 12
<212> TYPE: DNA
<213> ORGANISM: Artificial Sequence
<220> FEATURE:
<223> OTHER INFORMATION: tag sequence

<400> SEQUENCE: 36
tctaaaatta tt                                                         12

<210> SEQ ID NO 37
<211> LENGTH: 12
<212> TYPE: DNA
<213> ORGANISM: Artificial Sequence
<220> FEATURE:
<223> OTHER INFORMATION: tag sequence

<400> SEQUENCE: 37
tctaaaaaaa aa                                                         12

<210> SEQ ID NO 38
<211> LENGTH: 12
<212> TYPE: DNA
<213> ORGANISM: Artificial Sequence
<220> FEATURE:
<223> OTHER INFORMATION: tag sequence

<400> SEQUENCE: 38
gcaaaaatta aa                                                         12

<210> SEQ ID NO 39
<211> LENGTH: 12

```
<212> TYPE: DNA
<213> ORGANISM: Artificial Sequence
<220> FEATURE:
<223> OTHER INFORMATION: tag sequence

<400> SEQUENCE: 39
gcaaaaatta tt                                                       12

<210> SEQ ID NO 40
<211> LENGTH: 12
<212> TYPE: DNA
<213> ORGANISM: Artificial Sequence
<220> FEATURE:
<223> OTHER INFORMATION: tag sequence

<400> SEQUENCE: 40
aaaaaaaaaa aa                                                       12

<210> SEQ ID NO 41
<211> LENGTH: 32
<212> TYPE: DNA
<213> ORGANISM: Artificial Sequence
<220> FEATURE:
<223> OTHER INFORMATION: primer

<400> SEQUENCE: 41
atatgaaaaa aaaaaagac cctatgctga cc                                  32

<210> SEQ ID NO 42
<211> LENGTH: 33
<212> TYPE: DNA
<213> ORGANISM: Artificial Sequence
<220> FEATURE:
<223> OTHER INFORMATION: primer

<400> SEQUENCE: 42
agggtctttt tttttttca tatgtatatc tcc                                 33

<210> SEQ ID NO 43
<211> LENGTH: 32
<212> TYPE: DNA
<213> ORGANISM: Artificial Sequence
<220> FEATURE:
<223> OTHER INFORMATION: primer

<400> SEQUENCE: 43
atatggcaaa aattaaagac cctatgctga cc                                 32

<210> SEQ ID NO 44
<211> LENGTH: 33
<212> TYPE: DNA
<213> ORGANISM: Artificial Sequence
<220> FEATURE:
<223> OTHER INFORMATION: primer

<400> SEQUENCE: 44
agggtcttta attttgcca tatgtatatc tcc                                 33

<210> SEQ ID NO 45
<211> LENGTH: 32
<212> TYPE: DNA
<213> ORGANISM: Artificial Sequence
<220> FEATURE:
<223> OTHER INFORMATION: primer

<400> SEQUENCE: 45
```

```
atatgtctaa aaaaaaagac cctatgctga cc                                32

<210> SEQ ID NO 46
<211> LENGTH: 33
<212> TYPE: DNA
<213> ORGANISM: Artificial Sequence
<220> FEATURE:
<223> OTHER INFORMATION: primer

<400> SEQUENCE: 46
agggtctttt tttttagaca tatgtatatc tcc                               33

<210> SEQ ID NO 47
<211> LENGTH: 32
<212> TYPE: DNA
<213> ORGANISM: Artificial Sequence
<220> FEATURE:
<223> OTHER INFORMATION: primer

<400> SEQUENCE: 47
atatggcaaa aattattgac cctatgctga cc                                32

<210> SEQ ID NO 48
<211> LENGTH: 33
<212> TYPE: DNA
<213> ORGANISM: Artificial Sequence
<220> FEATURE:
<223> OTHER INFORMATION: primer

<400> SEQUENCE: 48
agggtcaata attttgcca tatgtatatc tcc                                33

<210> SEQ ID NO 49
<211> LENGTH: 32
<212> TYPE: DNA
<213> ORGANISM: Artificial Sequence
<220> FEATURE:
<223> OTHER INFORMATION: primer

<400> SEQUENCE: 49
atatgtctaa aattattgac cctatgctga cc                                32

<210> SEQ ID NO 50
<211> LENGTH: 33
<212> TYPE: DNA
<213> ORGANISM: Artificial Sequence
<220> FEATURE:
<223> OTHER INFORMATION: primer

<400> SEQUENCE: 50
agggtcaata attttagaca tatgtatatc tcc                               33
```